(12) United States Patent
Musallam et al.

(10) Patent No.: US 7,826,894 B2
(45) Date of Patent: Nov. 2, 2010

(54) COGNITIVE CONTROL SIGNALS FOR NEURAL PROSTHETICS

(75) Inventors: Sam Musallam, Pasadena, CA (US);
Richard A. Andersen, La Canada, CA (US); Brian D. Corneil, London (CA);
Bradley Greger, Van Nuys, CA (US);
Hansjorg Scherberger, Zurich (CH)

(73) Assignee: California Institute of Technology, Pasadena, CA (US)

( * ) Notice: Subject to any disclaimer, the term of this patent is extended or adjusted under 35 U.S.C. 154(b) by 559 days.

(21) Appl. No.: 11/086,534

(22) Filed: Mar. 22, 2005

(65) Prior Publication Data

US 2005/0228515 A1    Oct. 13, 2005

Related U.S. Application Data

(60) Provisional application No. 60/555,120, filed on Mar. 22, 2004.

(51) Int. Cl.
*A61B 5/04* (2006.01)
(52) U.S. Cl. .................. 600/544; 600/378; 600/545
(58) Field of Classification Search ................ 600/300, 600/544–546, 378; 706/12, 47; 623/24–25, 623/27, 57
See application file for complete search history.

(56) References Cited

U.S. PATENT DOCUMENTS

| | | | |
|---|---|---|---|
| 3,841,310 | A | 10/1974 | Goldstein |
| 4,314,379 | A | 2/1982 | Tanie et al. |
| 4,628,933 | A | 12/1986 | Michelson |
| 4,632,116 | A | 12/1986 | Rosen et al. |
| 4,878,913 | A | 11/1989 | Aebischer et al. |
| 4,926,969 | A | 5/1990 | Wright et al. |
| 4,949,726 | A | 8/1990 | Hartzell et al. |
| 5,037,376 | A | 8/1991 | Richmond et al. |

(Continued)

FOREIGN PATENT DOCUMENTS

EP    0 911 061 A2    4/1999

(Continued)

OTHER PUBLICATIONS

W. Wayt Gibbs, "Mind Readings," Scientific American, vol. 74, No. 1. Jun. 1996, pp. 34-36.

(Continued)

*Primary Examiner*—Max Hindenburg
*Assistant Examiner*—Rene Towa
(74) *Attorney, Agent, or Firm*—Seth D. Levy; Davis Wright Tremaine LLP

(57) ABSTRACT

In an embodiment, the invention relates to neural prosthetic devices in which control signals are based on the cognitive activity of the prosthetic user. The control signals may be used to control an array of external devices, such as prosthetics, computer systems, and speech synthesizers. Data obtained from monkeys' movement intentions were recorded, decoded with a computer algorithm, and used to position cursors on a computer screen. Not only the intended goals, but also the value of the reward the animals expected to receive at the end of each trial, were decoded from the recordings. The results indicate that brain activity related to cognitive variables can be a viable source of signals for the control of a cognitive-based neural prosthetic.

34 Claims, 12 Drawing Sheets

U.S. PATENT DOCUMENTS

| | | | |
|---|---|---|---|
| 5,178,161 A | | 1/1993 | Kovacs |
| 5,215,088 A | | 6/1993 | Normann et al. |
| 5,246,463 A | | 9/1993 | Giampapa |
| 5,314,495 A | | 5/1994 | Kovacs |
| 5,365,939 A | | 11/1994 | Ochs |
| 5,368,041 A | | 11/1994 | Shambroom |
| 5,406,957 A | | 4/1995 | Tansey |
| 5,413,103 A | | 5/1995 | Eckhorn |
| 5,571,057 A | * | 11/1996 | Ayers ........................ 463/36 |
| 5,638,826 A | * | 6/1997 | Wolpaw et al. ............ 600/544 |
| 5,687,291 A | | 11/1997 | Smyth |
| 5,692,517 A | | 12/1997 | Junker |
| 5,748,845 A | | 5/1998 | Labun et al. |
| 5,840,040 A | | 11/1998 | Altschuler et al. |
| 5,927,277 A | | 7/1999 | Baudino et al. |
| 6,097,981 A | | 8/2000 | Freer |
| 6,128,527 A | | 10/2000 | Howard, III et al. |
| 6,171,239 B1 | * | 1/2001 | Humphrey ................. 600/372 |
| 6,208,894 B1 | | 3/2001 | Schulman et al. |
| 6,216,119 B1 | | 4/2001 | Jannarone |
| 6,321,110 B1 | | 11/2001 | Ito et al. |
| 6,330,466 B1 | | 12/2001 | Hofmann et al. |
| 6,344,062 B1 | | 2/2002 | Abboudi et al. |
| 6,349,231 B1 | * | 2/2002 | Musha ....................... 600/544 |
| 6,516,246 B2 | | 2/2003 | Derakhshan |
| 6,546,378 B1 | | 4/2003 | Cook |
| 6,609,017 B1 | | 8/2003 | Shenoy et al. |
| 6,615,076 B2 | | 9/2003 | Mitra et al. |
| 6,952,809 B2 | * | 10/2005 | Beranek et al. ............ 715/856 |
| 7,275,035 B2 | * | 9/2007 | Kennedy .................... 704/271 |
| 2002/0016638 A1 | * | 2/2002 | Mitra et al. .................... 623/24 |
| 2002/0103429 A1 | | 8/2002 | DeCharms |
| 2002/0107454 A1 | | 8/2002 | Collura et al. |
| 2003/0023319 A1 | * | 1/2003 | Andersen et al. ............. 623/24 |
| 2003/0093129 A1 | * | 5/2003 | Nicolelis et al. .............. 607/45 |
| 2003/0105409 A1 | * | 6/2003 | Donoghue et al. .......... 600/545 |

FOREIGN PATENT DOCUMENTS

| | | |
|---|---|---|
| WO | 00/09008 A | 2/2000 |
| WO | 00/33731 A1 | 6/2000 |
| WO | 01/43635 A1 | 6/2001 |
| WO | 03/000161 A1 | 1/2003 |

OTHER PUBLICATIONS

Dr. Richard K. Eisley, "Adaptive Control of Prosthetic Limbs Using Neural Networks," IJCNN Joint Conference on Neural Networks, 1990, pp. II-771-776.

Eisley et al., "Application of Neural Networks to Adaptive Control," 1988.

Snyder, L.H. et al., "Coding of Intention in the Posterior Parietal Cortex," Nature, Mar. 13, 1997, 386:167-70.

Zipser, D and Andersen, RA, "A Back-Propagation Programmed Network that Simulates Response Properties of a Subset of Posterior Parietal Neurons," Nature, Feb. 25, 1988, 331 (6158):679-84.

Clower, DM. et al., "Role of Posterior Parietal Cortex in the Recalibration of Visually Guided Reaching," Nature, Oct. 17, 1996, 383(6601):618-21.

Galleti, C. et al., "Short Communication Arm Movement-related Neurons in the Visual Area V6A of the Macaque Superior Parietal Lobule," European Journal of Neuroscience, Feb. 1997, 9(2):410-3.

Johnson, PB., et al., "Cortical Networks for Visual Reaching: Physiological and Anatomical Organization of Frontal and Parietal Lobe Arm Regions," Cerebral Cortex, Mar./Apr. 1996, 6:102-19.

Lukashin, AV et al., "A Simulated Actuator Driven by Motor Cortical Signals" NeuroReport, Nov. 1996, 7 (15-17):2597-601.

Sciences, Lynch,JC. et al., "The Functional Organization of Posterior Parietal Association Cortex," The Behavioral and Brain Sciences, Dec. 1980, 3(4):485-534.

Murthy VN and Fetz EE; Oscillatory Activity in Sensorimotor Cortex of Awake Monkeys: Synchronization of Local Field Potentials and Relation to Behavior; Dec. 1996; Journal of Neurophysiology, vol. 76, No. 6, pp. 3949-3967.

Murthy VN and Fetz EE Synchronization of Neurons During Local Field Potential Oscillations in Sensorimotor Cortex of Awake Monkeys; Dec. 1996; Journal of Neurophysiology, vol. 76, No. 6; pp. 3968-3982.

Cook et al., "Development of a Robotic Device for Facilitating Learning by Children Who Have Severe Disabilities," IEEE Transactions on Neural Systems and Rehabilitation Engineering, Sep. 2002.

Salinas et al. "Transfer of Coded Information from Sensory to Motor Networks," J. Neurosci. 1995, 15:6461:6474.

Batista, A.P. et al. "Reach plan in eye centered coordinates" Science Jul. 9, 1999, vol. 285, pp. 257-260.

Haugland et al. "Artifact free sensory nerve signals obtained from cuff electrodes during electrical stimulation of nearby muscles," IEEE Transactions on Rehabilitation Engineering, vol. 2, No. 1, Mar. 1994, pp. 37-40.

Salinas, E and Abbott, LF "Vector reconstruction from firing rates," Journal of Computational Neuroscience, 1994, 1:89-107.

Zhang, K et al. "Interpreting Neuronal population activity by reconstruction: unified framework with application to hippocampal place cells," Journal of Neurophysiology, Feb. 1998, 79(2):1017-1044.

Brown, EN et al. "A statistical paradigm for neural spike train decoding applied to position prediction from ensemble firing patterns of rat hippocampal place cells," The Journal of Neuroscience, Sep. 15, 1998, 18(18):7411-25.

Buonomano, DV et al. "Cortical plasticity: from synapses to maps," Annual Review of Neuroscience, 1998, 21:49-86.

Colby, CL "Action-oriented spatial reference frames in cortex" Neuron, Jan. 1998, 20:15-24.

Hatsopoulos, NG et al. "Information about movement direction obtained from synchronous activity of motor cortical neurons," Proc. Natl. Acad. Sci. USA, Dec. 1998, 95:15706-11.

Sanes, JN et al. "Oscillations in local field potentials of the primate motor cortex during voluntary movement," May 1993, Proc. Natl. Acad. Sci. USA, vol. 90, pp. 4470-4474.

Donoghue, JP et al. "Neural discharge and local field potential oscillations in primate motor cortex during voluntary movements," pp. 159-173.

Smith et al. "An artificial neural network model of certain aspects of fighter pilot cognition," IEEE International Conference on Decision Aiding for Complex Systems, Oct. 13-16, 1991.

Buneo, CA et al. (2002). "Direct visuomotor transformations for reaching," Nature 416:632-636.

Cohen, YE et al. (2002). "Comparison of neural activity preceding reaches to auditory and visual stimuli in the parietal reach region," NeuroReport 13:891-894.

Grunewald, A et al. (2002) "Neural correlates of structure-from-motion perception in macaque V1 and MT," J. Neurosci. 22:6195-6207.

Pesaran, B et al. (2002) "Temporal structure in neuronal activity during working memory in Macaque parietal cortex," Nature Neuroscience 5: 805-811.

Sabes, PN et al. (2002) "The parietal representation of object-based saccades," J. Neurophysiol. 88: 1815-1829.

Shenoy, KV et al. (2002) "Pursuit speed compensation in cortical area MSTd," J. Neurophysiol. 88:2630-2647.

Sugihara, H et al. (2002) "Responses of MSTd neurons to simulated 3D-orientation of rotating planes," J. Neurophysiol. 87:273-285.

Andersen, RA et al. (2002) "Intentional maps in posterior parietal cortex," Ann.Rev.Neurosci 25:189-200.

Cohen, YE et al. (2002) "A common reference frame for movement plans in the posterior parietal cortex," Nature Review Neuroscience 3:553-562.

Scherberger, H et al. (2002) "Sensorimotor transformation in the posterior parietal cortex," The Visual Neurosciences, Cambridge, MA, MIT Press, 1324-1336.

Batista, AP et al. (2001) "The parietal reach region codes the next planned movement in a sequential reach task," J. Neurophysiol. 85(2):539-544.

Crowell, JA et al. (2001) "Pursuit compensation during self-motion," Perception 30:1465-1488.

Dubowitz, DJ et al. (2001) "Direct comparison of visual cortex activation in human and non-human primates using functional magnetic resonance imaging," J. Neurosci. Methods 107:71-80.

Dubowitz, DJ et al. (2001) "Enhancing fMRI contrast in awake behaving primates using intravascular magnetite Dextran Nanoparticles," NeuroReport 12:2335-2340.

Jarvis, MR et al. "Sampling properties of the spectrum and coherency of sequences of action potentials," Neural Computation, 13(4):717-749 Apr. 2001.

Li, C-S et al. (2001) "Inactivation of macaque area LIP delays initiation of the second saccade from contralesional eye positions in a double-saccade task," Exp. Brain Res. 137:45-57.

Cohen, YE et al. (2000) "Reaches to sounds encoded in an eye-centered reference frame," Neuron 27:647-652.

Desouza, JFX et al. (2000) "Eye position signal modulates a human parietal pointing region," J. Neurosci. 20:5835-5840.

Snyder, LH et al. (2000) "Saccade-related activity in the parietal reach region," J. Neurophysiol. 83:1099-1102.

Xing, J et al. (2000) "Models of posterior parietal cortex which perform multimodal integration and represent space in several coordinate frames," J. Cognitive Neurosci. 12:601-614.

Xing, J et al. (2000) "The memory activity of LIP neurons in sequential eye movements simulated with neural networks," J. Neurophysiol. 84:651-665.

Snyder, LH et al. (2000) "Intention-related activity in the posterior parietal cortex: a review," Vision Res. 40:1433-1441.

Branchaud, EA et al. "A miniature robot that autonomously optimizes and maintains extracellular neural action potential recordings," Proceedings of the 2005 Int'l Conf. Robotics and Automation.

Takahashi, M et al. Neural Network for Human Cognitive State Estimation IEEE International Conference on Advanced Robotic System, and the Real World, Sep. 12-16, 1994.

Andersen, RA et al. (2003) "Sensorimotor integration in posterior parietal cortex," Advances in Neurology vol. 93—The Parietal Lobes, Siegal, AM, Andersen, RA, Freund H and Spencer DD, Philadelphia, Lippincott Williams & Wilkins, 159-179.

Scherberger, H et al. (2005). "Cortical Local Field Potential Encodes Movement Intentions in the Posterior Parietal Cortex." Neuron. 46:347-354.

Campos, M et al. (2005). "The Supplementary Motor Area Encodes Reward Expectancy in Eye Movement Tasks." J. Neurophysiol. 94:1325-1335.

Rizzuto, D et al. (2005). "Spatial Selectivity in Human Ventrolateral Prefrontal Cortex." Nature Neuroscience. 8:4:415-417.

Cham, JG et al. (2005). "Semi-chronic Motorized Microdrive and Control Algorithm for Autonomously Isolating and Maintaining Optimal Extracellular Action Potentials." J. Neurophysiol. 93:570-579, 2005.

Pang, C et al. (2005). "A New Multi-Site Probe Array with Monolithically Integrated Parylene Flexible Cable for Neural Prostheses." Proceedings of the 27th Annual International Conference of the IEEE Engineering in Medicine and Biology Society.

Andersen, RA et al. (2005). "Cognitive Based Neural Prosthetics." Proceedings of the 2005 Intl. Conf. Robotics and Automation.

Buneo CA et al. "The posterior parietal cortex: Sensorimotor interface for the planning and online control of visually guided movements," Neuropsychologia. Nov. 18, 2005.

Andersen, RA et al. "Selecting the signals for a brain-machine interface," Curr Opin Neurobiol. Dec. 2004; 14 (6):720-6.

Andersen, RA et al. "Cognitive neural prosthetics," Trends Cogn Sci Nov. 2004; 8(11):486-93.

Buneo, CA et al. "Properties of spike train spectra in two parietal reach areas," Exp Brain Res. Nov. 2003; 153 (2):134-9. Epub Aug. 28, 2003.

Pesaran, B et al. "Dorsal premotor neurons encode the relative position of the hand, eye, and goal during reach planning." Neuron. Jul. 6, 2006; 51(1):125-34.

Quiroga, QR et al. "Movement intention is better predicted than attention in the posterior parietal cortex" J. Neurosci. Mar. 29, 2006; 26(13):3615-20.

Musallam, S et al. "Cognitive control signals for neural prosthetics." Science Jul. 9, 2004; 305 (5681):258-62.

Corneil, BD et al. "Dorsal neck muscle vibration induces upward shifts in the endpoints of memory-guided saccades in monkeys." J Neurophysiol. Jul. 2004; 92(1):553-66. Epub Mar. 3, 2004.

Scherberger, H et al. "Magnetic resonance image-guided implantation of chronic recording electrodes in the macaque intraparietal sulcus." J Neurosci Methods Nov. 30, 2003; 130(1):1-8.

Connolly, JD et al. "FMRI evidence for a 'parietal reach region' in the human brain." Exp Brain Res. Nov. 2003; 153 (2):140-5. Epub Sep. 4, 2003.

Andersen, RA et al. (2004) "Recording Advances for Neural Prosthetics," Proceedings of the 26th Annual International Conference of the IEEE IMBS, San Francisco, CA, USA, Sep. 1-5, 2004, 5352-5355.

Engenious. By Pure Thought Alone: The Development of the First Cognitive Neural Prosthesis by Burdick, JW and Andersen, RA, Pasadena, CA, Caltech, 2004.

Andersen, et al. (2004) "Sensorimotor Transformations in the Posterior Parietal Cortex," The Cognitive Neurosciences III, Ed. MS Gazzaniga, Cambridge, MA:MIT P:2004, 463-474.

Cohen, YE et al. (2004). "Multimodal spatial representations in the primate parietal lobe," Crossmodal Space and Crossmodal Attention, J. Driver and C. Spence (Eds.) pp. 99-122, Oxford University Press.

Cohen, YE et al. (2004). "Multisensory representations of space in the posterior parietal cortex," In: Handbook of Multisensory Integration, G. Calvert, C. Spence, and B. Stein (Eds.), pp. 463-479, MIT Press, Cambridge, MA.

Mojarradi, M et al. (2003). "A miniaturized neuroprosthesis suitable for implants into the brain," IIEE Transactions on Neural Systems and Rehabilitation Engineering 11:1534-4320.

Nishida, S et al. (2003) "Gaze modulation of visual aftereffects," Vision Research 43:639-649.

Scherberger, H et al. (2003) "Target selection for reaching and saccades share a similar behavioral reference frame in the macaque," J. Neurophysiol. 89:1456-1466.

Shenoy, KV et al. (2003). "Neural prosthetic control signals from plan activity," NeuroReport 14:591-597.

Dotsinsky, I.A. et al., Multichannel DC amplifier for a microprocessor electroencephalograph, Medical and Biological Engineering and Computing, May 1, 1991, vol. 29, pp. 324-329.

JI, J. et al., An implantable CMOS analog signal processor for multiplexed microelectrode recording arrays, IEEE, Feb. 24, 1990, pp. 107-110.

Schwartz, A.B. et al., Brain-Controlled Interfaces: Movement Restoration with Neural Prosthetics, Neuron, vol. 52, pp. 205-220 (Oct. 5, 2006).

Mountcastle, V.B., The columnar organization of the neocortex, Brain, vol. 120, pp. 701-722 (1997).

Kandel, E.R. et al., Principles of Neural Science, 4th Ed., McGraw-Hill, New York, p. 916 (2000).

Donoghue, J.P., Connecting cortex to machines: recent advances in brain interfaces, Nature Neuroscience, 5:1085-1088 (2002).

Corneil, B. D. et al.; Abstract: Representation of reward expectancy in the medial bank of the intraparietal suclus: implications for neural prosthetics, Session No. 607.8 2003 Neuroscience Meeting Planner. Nov. 11, 2003. New Orleans, LA.

Musallum, S., et al. Abstract: Real time control of a cursor using multi-electrode arrays implanted in the medial bank of the intraparietal sulcus., Session No. 607.7 2003 Neuroscience Meeting Planner. Nov. 11, 2003. New Orleans, LA.

Corneil, B.D., et al. Poster: Representation of reward expectancy in the medial bank of the intrapareital suclus: implications for neural prosthetics, #607.8. 2003 Neuroscience Meeting Planner. Nov. 11, 2003. New Orleans, LA.

Musallum, S., et al. Poster: Real time control of a cursor using multi-electrode arrays implanted in the medial bank of the intraparietal sulcus., #607.7. 2003 Neuroscience Meeting Planner. Nov. 11, 2003. New Orleans, LA.

* cited by examiner

COGNITIVE CONTROL SIGNALS FOR NEURAL PROSTHETICS

CROSS REFERENCE TO RELATED APPLICATIONS

This application claims the benefit of priority from U.S. Provisional Application Ser. No. 60/555,120, filed Mar. 22, 2004.

GOVERNMENT RIGHTS

The U.S. Government has certain rights in this invention pursuant to Grant No. RO1 EY013337 awarded by the National Institutes of Health; Grant No. N00014-01-1-0035 awarded by the Office of Naval Research; and Grant No. MDA972-00-1-0029 awarded by the Defense Advanced Research Projects Agency.

BACKGROUND

Many limb prostheses operate in response to muscle contractions performed by the user. Some prostheses are purely mechanical systems. For example, a type of lower limb prosthesis operates in response to the motion of the residual limb. When the user's thigh moves forward, inertia opens the knee joint of the prosthesis, an artificial shin swings forward, and, when the entire structure locks, the user may pass his or her weight over the artificial leg. Other prostheses may incorporate electric sensors to measure muscle activity and use the measured signals to operate the prosthesis.

Such prostheses may provide only crude control to users that have control over some remaining limb musculature, and hence may not be useful for patients with spinal damage. For these patients, it may be desirable to measure precursor signals coded for limb movement in the patient's brain, and then decode these signals to determine the intended movement and/or target. A similar approach can be applied to patients with paralysis from a range of causes including peripheral neuropathies, stroke, and multiple sclerosis. The decoded signals could be used to operate pointing external devices such as a computer, a vehicle, or a robotic prosthesis.

BRIEF DESCRIPTION OF THE DRAWINGS

These and other aspects will now be described in detail with reference to the following drawings.

Like reference symbols in the various drawings indicate like elements.

DETAILED DESCRIPTION

All references cited herein are incorporated by reference in their entirety as if fully set forth.

Current studies that record the spike activity of neurons have focused primarily on deriving hand trajectory signals primarily, but not exclusively, from the motor cortex. Recordings from the cells are "decoded" to control the trajectories of a robotic limb or a cursor on a computer screen. Electroencephalogram (EEG)-based signals have also been used to derive neuroprosthetic commands.

In an embodiment, cognitive control signals are derived from higher cortical areas related to sensory-motor integration in the parietal and frontal lobes. The primary distinction between cognitive signals from other types of signals, e.g., from the motor cortex, is not the location from which recordings are made, but rather the type of information being decoded and the strategy for using these signals to assist patients.

Cognitive signals are characterized as lying in the spectrum between pure sensory signals at the input, e.g., reflex due to light shined in an individual's eye, and motor signals at the output, e.g., signals used to execute a reach. Cognitive signals can result in neural activity in the brain even in the absence of sensory input or motor output. Examples of cognitive signals include abstract thoughts, desires, goals, trajectories, attention, planning, perception, emotions, decisions, speech, and executive control.

Figure 1:
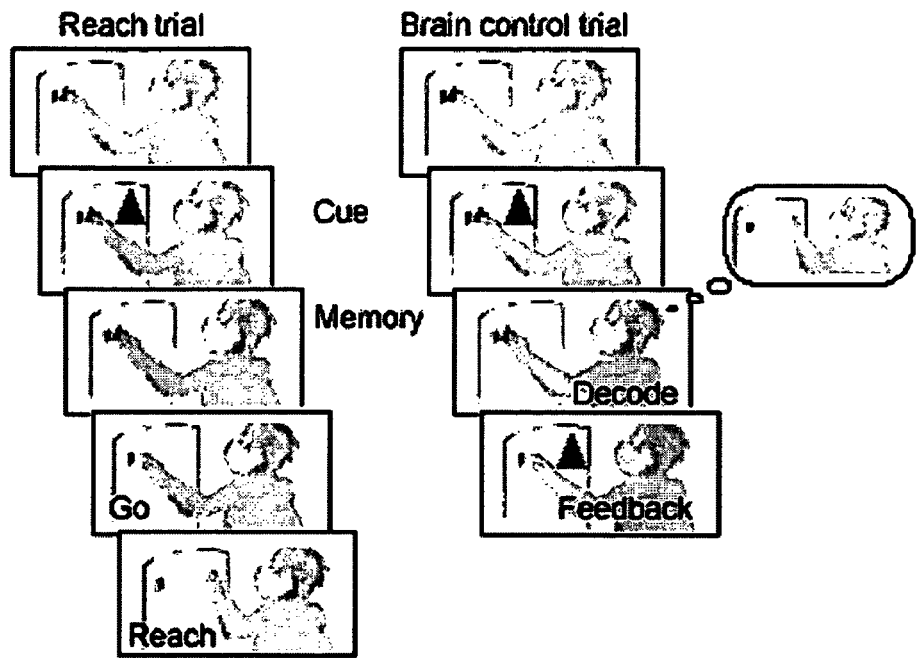
FIG. 1 illustrates tasks for reach and brain control trials in accordance with an embodiment of the present invention. At 500 ms after the monkeys touched a central green cue and looked at a central fixation point (red), a peripheral cue (green) was flashed for 300 ms. For reach trials, the monkeys were rewarded if they reached to the target at the end of a memory period of 1500±300 ms. During brain control trials, data from 200 to 1100 ms of the memory period was used to decode the intended reach location. Monkeys were rewarded if the correct target was decoded.

Experiments have recently been performed in monkeys in which reach intentions are decoded from neural activity in real time, and used to position a cursor on a computer screen—the so-called brain-control task, as shown in FIG. 1. Arrays of electrodes were placed in the medial intraparietal area (MIP), a portion of the parietal reach region (PRR), area 5 (also in the posterior parietal cortex), and the dorsal premotor cortex (PMd).

PRR in non-human primates lies within a broader area of cortex, the posterior parietal cortex (PPC). The PPC is located functionally at a transition between sensory and motor areas and is involved in transforming sensory inputs into plans for action, so-called sensory-motor integration. The PPC contains many anatomically and functionally defined subdivisions.

Of particular interest in recent years are areas within the intraparietal sulcus that are involved in planning eye movements (the lateral intraparietal area, LIP), reach movements (PRR), and grasping (the anterior intraparietal area, AIP). PRR has many features of a movement area, being active primarily when a subject is preparing and executing a movement. However, the region receives direct visual projections and vision is perhaps its primary sensory input. Moreover, this area codes the targets for a reach in visual coordinates relative to the current direction of gaze (also called retinal or eye-centered coordinates). Similar visual coding of reaches has been reported in a region of the superior colliculus.

This coding in visual coordinates underscores the cognitive nature of the planning signal within PRR. It is coding the desired goal of a movement, rather than the intrinsic limb variables required to reach to the target. Moreover, PRR can hold the plan for a movement in short-term memory through persistent activity of its neurons. This intention-related activity provides a useful neural correlate of the intentions of the subject for subsequent decoding. The human homologue of PRR has recently been identified in FMRI experiments. Less is currently known about the coordinates for coding in PMd. However, studies indicate that at least a subset of cells has properties similar to those found in PRR.

One advantage of using high level cortical areas like PRR as a target for a cortical prosthetic is the visual nature of the area. Somatosensory feedback regarding the outcome of a movement is often lost with paralysis, but vision generally remains intact. Thus PRR can receive a very direct visual "error signal" for learning to operate a neural prosthetic in the face of paralysis. PRR is also more anatomically remote from the somatosensory and motor pathways that are damaged in paralysis. It is possible that PRR will show less degeneration than is seen in other cortical areas as a result of the loss of these pathways.

The use of cognitive signals also has the advantage that many of these signals are highly plastic, can be learned quickly, are context dependent, and are often under conscious control. Consistent with the extensive cortical plasticity of cognitive signals, the animals learned to improve their performance with time using PRR activity. This plasticity is important for subjects to learn to operate a neural prosthetic. The time course of the plasticity in PRR is in the range of one or two months, similar to that seen in motor areas for trajectory decoding tasks. Moreover, long-term, and particularly short-term, plasticity is a cognitive control signal that can adjust brain activity and dynamics to allow more efficient operation of a neural prosthetic device.

In addition, short term improvements in performance were achieved by manipulating the expected value of reward. The expected value of the probability of reward, the size of the reward and the type of reward were decoded from the activity in the brain control experiments. The finding of these signals in PRR is new, and parallels similar finding of expected value in nearby area LIP as well as other cortical and subcortical areas. This activity does not appear to be linked to attention since PRR is active selectively for reach plans and did not show an enhancement of activity to aversive reward trials.

Figure 9:
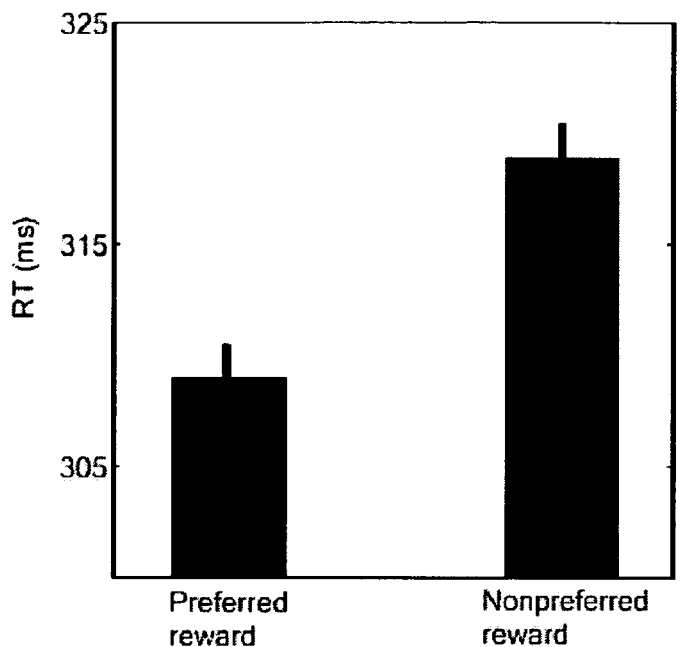
FIG. 9 is a graph showing the reach reaction time for preferred (n=6671 reaches) and non-preferred (n=7180 reaches) conditions for monkeys S and C, respectively, in accordance with an embodiment of the present invention. Bars are SE.

The correlation of increased activity with increased expected reward is substantiated by behavioral data that showed a decrease in reaction times for the preferred rewards, as shown in FIG. 9. Expected value is a necessary component of the neural system that mediates decision making. On the other hand, it is also possible that we are seeing motivational effects that are a direct consequence of expected value.

The decoding of intended goals is an example of the use of cognitive signals for prosthetics. Once these goals are decoded, then smart external devices can perform the lower level computations necessary to obtain the goals. For instance, a smart robot can take the desired action and can then compute the trajectory. This cognitive approach is very versatile because the same cognitive/abstract commands can be used to operate a number of devices. The decoding of expected value also has a number of practical applications, particularly for patients that are locked in and cannot speak or move. These signals can directly indicate, on-line and in parallel with their goals, the preferences of the subject and their motivational level and mood. Thus they could be used to assess the general demeanor of the patient without constant querying of the individual (much like one assesses the body-language of another). These signals could also be rapidly manipulated to expedite the learning that patients must undergo in order to use an external device. Moreover, different kinds of cognitive signals can be decoded from patients. For instance, recording thoughts from speech areas could alleviate the use of more cumbersome letter-boards and time consuming spelling programs. Or recordings from emotion centers could provide an on-line indication of the subjects' emotional state. Recording from areas of the brain involved in executive control, particularly cortical areas of the frontal lobe, can provide abstract associations of objects with actions as well as allow long-term planning signals to be utilized for control and programming.

The cognitive-based prosthetic concept is not restricted for use to a particular brain area. However, some areas will no doubt be better than others depending on the cognitive control signals that are required. Future applications of cognitive based prosthetics will likely record from multiple cortical areas in order to derive a number of variables. Other parts of the brain besides cortex also contain cognitive related activity and can be used as a source of signals for cognitive control of prosthetics. Finally, the cognitive-based method can easily be combined with motor-based approaches in a single prosthetic system, reaping the benefits of both.

Figure 2:
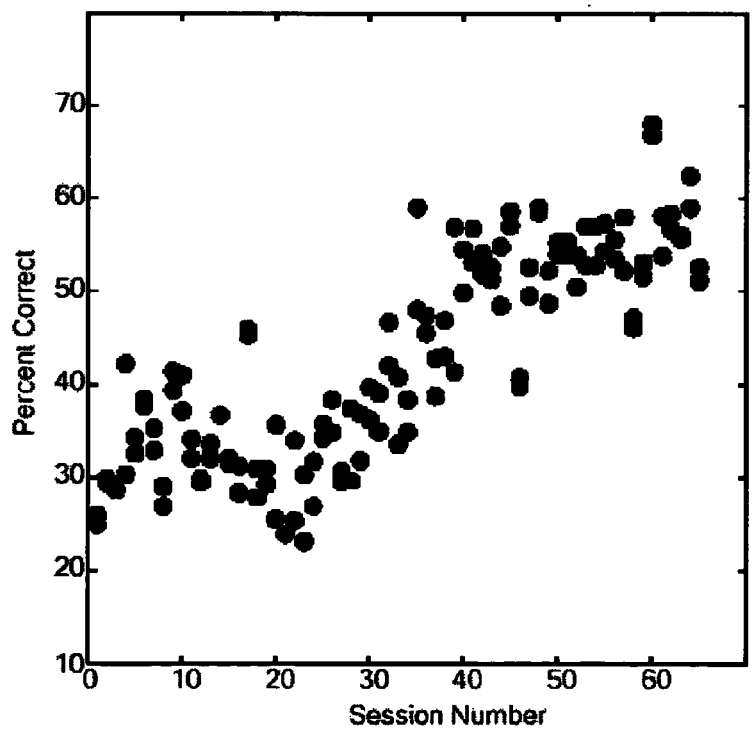
FIG. 2 is a plot showing off-line decode results performed with an adaptive and a frozen database for all the parietal reach region (PRR) recording sessions in consecutive order for monkey S in accordance with an embodiment of the present invention. No statistical difference exists between the two populations.

An advantage of cognitive control signals is that they do not require the subject to make movements to build a database for predicting the subjects thoughts. This would of course be impossible for paralyzed patients. This point was directly addressed in off-line analysis by comparing the performance between "adaptive" and "frozen" databases, described in greater detail in the ensuing Experimental Results. With the adaptive database, each time a successful brain-control trial was performed it was added to the database, and because the database was kept at the same number of trials for each direction, the earliest of the trials is dropped. Eventually only brain-control trials are contained within the database. In the case of the frozen database, the reach data was used throughout the brain-control segment. Both decodes were performed with the same data. As can be seen in FIG. 2, both databases produce the same performance. Thus paralyzed patients can be simply asked to plan to make a reach and this planning activity can be used to build a database even though the patients cannot actually reach.

Signals related to reward prediction are found in several brain areas. PRR cells are more active and better tuned when the animal expects higher probability of reward at the end of a successful trial. PRR cell activity also shows a reward preference, being more active before the expected delivery of a preferred citrus juice reward than a neutral water reward. The expected value in brain-control experiments could be read out simultaneously with the goal using off-line analysis of the brain control trials. These experiments show that multiple cognitive variables can be decoded at the same time.

As described in U.S. Pat. No. 6,615,076, it has recently been found that the local field potentials (LFP) recorded in the posterior parietal cortex of monkeys contains a good deal of information regarding the animals' intentions. In an embodiment, the LFP may be recorded in addition to, or instead of, single unit activity (SU) and used to build the database(s) for cognitive signals and decode the subject's intentions. These LFP signals can also be used to decode other cognitive signals such as the state of the subject. Moreover, the same cognitive signals that can be extracted with spikes can also be extracted with LFPs and include abstract thoughts, desires, goals, trajectories, attention, planning, perception, emotions, decisions, speech, and executive control.

In one embodiment, an electrode may be implanted into the cortex of a subject and used to measure the signals produced by the firing of a single unit (SU), i.e., a neuron, in the vicinity of an electrode. The SU signal may contain a high frequency component. This component may contain spikes-distinct events that exceed a threshold value for a certain amount of time, e.g., a millisecond. Spikes may be extracted from the signal and sorted using known spike sorting methods.

Attempts have been made to use the spike trains measured from particular neurons to predict a subject's intended movements. The predicted intention could then be used to control a prosthetic device. However measuring a spike train with a chronic implant and decoding an intended movement in real time may be complicated by several factors.

In general, measuring SU activity with a chronic implant may be difficult because the SU signal may be difficult to isolate. An electrode may be in the vicinity of more than one neuron, and measuring the activity of a target neuron may be affected by the activity of an adjacent neuron(s). The implant may shift position in the patient's cortex after implantation, thereby changing the proximity of an electrode to recorded neurons over time. Also, the sensitivity of a chronically implanted electrode to SU activity may degrade over time.

LFP is an extracellular measurement that represents the aggregate activity of a population of neurons. The LFP measured at an implanted electrode during the preparation and execution of a task has been found to have a temporal structure that is approximately localized in time and space. Information provided by the temporal structure of the LFP of neural activity appears to correlate to that provided by SU activity, and hence may be used to predict a subject's intentions. Unlike SU activity, measuring LFP activity does not require isolating the activity of a single unit. Accordingly, it may be advantageous to use LFP activity instead of, or in conjunction with SU activity to predict a subject's intended movement in real time.

Figure 13:
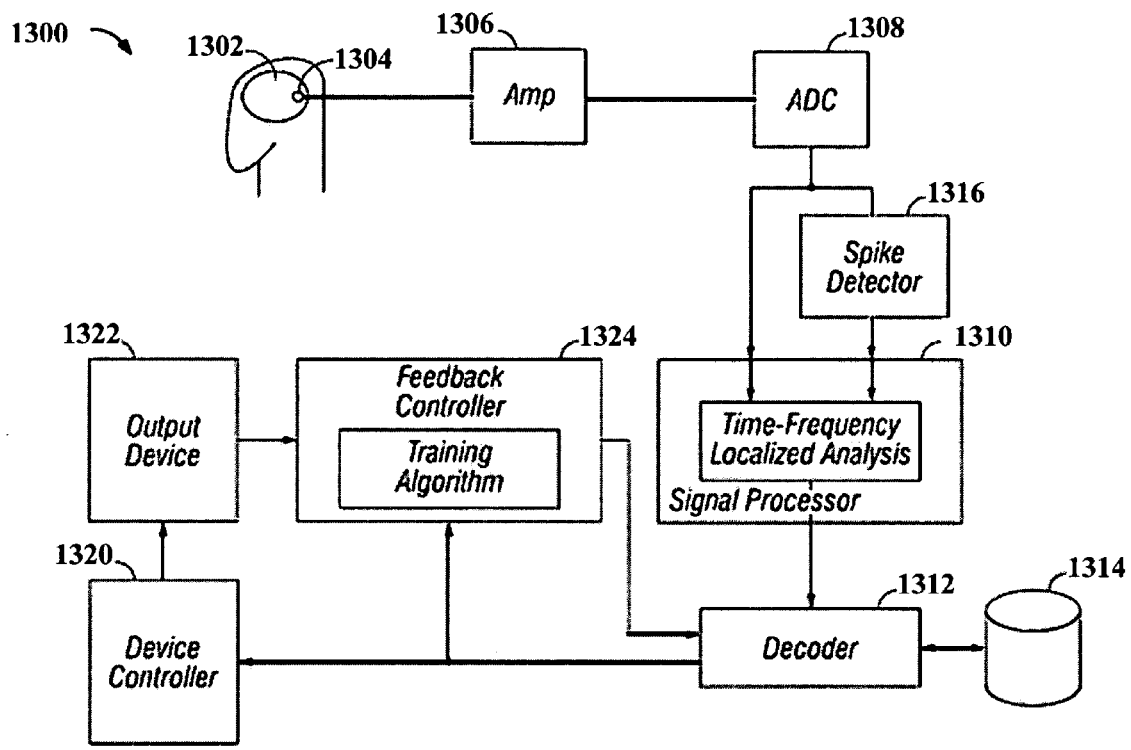
FIG. 13 is a block diagram of a neural prosthetic system utilizing cognitive control signals according to an embodiment of the present invention.

Although experiments were conducted on the posterior parietal reach region (PRR) and the dorsal premotor cortex (PMd), similar approaches can be used for interpreting cognitive signals from other brain areas. It is likely that some areas will be better than others depending on the cognitive signals to be decoded and the parts of the brain that are damaged System FIG. 13 illustrates a system 1300 that uses cognitive signals to predict a subject's intended movement plan or other cognitive signal. The activity of neurons in the subject's brain 1302 may be recorded with an implant 1304. The implant 1304 may include an array of electrodes that measure the action potential (SU) and/or extracellular potential (LFP) of cells in their vicinity. In one embodiment, micro-electromechanical (MEMS) technology may be used to prepare a movable electrode array implant. In alternate embodiments, the neural activity may be measured in forms other than electrical activity. These include, for example, optical or chemical changes, or changes in blood flow that may be measured by suitable measuring devices.

Neural activity measured with the implant 1304 may be amplified in one or more amplifier stages 1306 and digitized by an analog-to-digital converter (ADC) 1308. In an embodiment, multiple implants may be used. Recordings may be made from multiple sites in a brain area, with each brain site carrying different information, e.g., reach goals, intended value, speech, abstract thought, executive control. The signals recorded from different implants may be conveyed on multiple channels.

The measured waveform(s), which may include frequencies in a range having a lower threshold of about 1 Hz and an upper threshold of from 5 kHz to 20 kHz may be filtered as an analog or digital signal into different frequency ranges. For example, the waveform may be filtered into a low frequency range of say 1-20 Hz, a mid frequency range of say 15-200 Hz, which includes the beta (15-25 Hz) and gamma (25-90 Hz) frequency bands, and a high frequency range of about 200 Hz to 1 kHz, which may include unsorted spike activity. In an alternate embodiment, the digitized signal may also be input to a spike detector 1316 which may detect and sort spikes using known spike sorting operations.

The digitized LFP signal, and the sorted spike signal if applicable, may be input to a signal processor 1310 for time-frequency localized analysis.

The signal processor 1310 may estimate the spectral structure of the digitized LFP and spike signals using multitaper methods. Multitaper methods for spectral analysis provide minimum bias and variance estimates of spectral quantities, such as power spectrum, which is important when the time interval under consideration is short. With multitaper methods, several uncorrelated estimates of the spectrum (or cross-spectrum) may be obtained from the same section of data by multiplying the data by each member of a set of orthogonal tapers. A variety of tapers may be used. Such tapers include, for example, parzen, Hamming, Hanning, Cosine, etc. An implementation of a multitaper method is described in U.S. Pat. No. 6,615,076, which is incorporated by reference herein in its entirety.

In an alternate embodiment the temporal structure of the LFP and SU spectral structures may be characterized using other spectral analysis methods. For example, filters may be combined into a filter bank to capture temporal structures localized in different frequencies. As an alternative to the Fourier transform, a wavelet transform may be used to convert the date from the time domain into the wavelet domain. Different wavelets, corresponding to different tapers, may be used for the spectral estimation. As an alternative to calculating the spectrum on a moving time window, nonstationary time-frequency methods may be used to estimate the energy of the signal for different frequencies at different times in one operation. Also, nonlinear techniques such as artificial neural networks (ANN) techniques may be used to learn a solution for the spectral estimation.

The signal processor 1310 may generate a feature vector train, for example, a time series of spectra of LFP, from the input signals. The feature vector train may be input to a decoder 1312 and operated on to decode the subject's cognitive signal, and from this information generate a high level control signal.

The decoder 1312 may use different predictive models to determine the cognitive signal. These may include, for example: probabilistic; Bayesian decode methods (such those described in Zhang, K., Ginzburg, I., McNaughton, B. L., and Sejnowski, T. J. (1998), Interpreting Neuronal population Activity by Reconstruction: Unified Framework with Application to Hippocampal place cells. J Neurophysiol 79:1017-1044); population vector models (such as those described in Lukashin, A. V., Amirikian, B. R., and Georgopoulos, A. P. (1996). A Simulated Actuator Driven by Motor Cortical Signals. Neuroreport 7(15-17):2597-2601); and artificial neural networks.

The decoder 1312 may use a derived transformation rule to map a measured neural signal, s, into an action, a, for example, a target. Statistical decision theory may be used to derive the transformation rule. Factors in the derivations may include the set of possible neural signals, S, and the set of possible actions, A. The neuro-motor transform, d, is a mapping for S to A. Other factors in the derivation may include the intended target .theta. and a loss function which represents the risk associated with taking an action, a, when the true intention was θ. These variables may be stored in a memory device, e.g., a database 1314.

Two approaches may be used to derive the transformation rule: a probabilistic approach, involving the intermediate step of evaluating a probabilistic relation between s and θ and subsequent minimization of an expected loss to obtain a neuro-motor transformation (i.e., in those embodiments of the invention that relate to intended movement rather than, e.g., emotion); and a direct approach, involving direct construction of a neuro-motor transformation and minimizing the empirical loss evaluated over the training set. In terms of so-called "neural network" functions, the second approach may be regarded as defining a neural network with the neural signals as input and the target actions as output, the weights being adjusted based on training data. In both cases, a critical role is played by the loss function, which is in some sense arbitrary and reflects prior knowledge and biases of the investigator.

As described above, the measured waveform(s) may be filtered into a low frequency range of say 1-20 Hz, a mid frequency range of say 15-200 Hz, which includes the beta (15-25 Hz) and gamma (25-90 Hz) frequency bands, and a high frequency range of about 200 Hz to 1 kHz, which may include unsorted spike activity. The decoder 1312 may decode a cognitive signal using the information in the gamma frequency band (25-90 Hz) of the LFP spectra and the SU spectra. The decoder 1312 may decode logical signals using information in the gamma (25-90 Hz) and beta (15-25 Hz)

frequency bands of the LFP spectra and the SU spectra. The logical information may include a decision to execute an action, e.g., a "GO" signal. The logical information may indicate that the subject is entering other states, such as cuing a location, preparing to execute an action, and scrubbing a planned action.

Once the decoder 1312 maps the feature vectors from the signal processor 1310 to an action, the decoder 1312 may generate a high level signal indicative of the cognitive signal and transmit this signal to the device controller 1320. The device controller 1320 may use the signal to control the output device 1322 to, e.g., mimic the subject's intended movement or perform another task associated with the cognitive signal. The output device may be, for example, a robotic limb, an animated limb or a pointing device on a display screen, or a functional electrical stimulation device implanted into the subject's muscles for direct stimulation and control.

The decoder 1312 may need to be recalibrated over time. This may be due to inaccuracies in the initial calibration, degradation of the implant to spike activity over time, and/or movement of the implant, among other reasons.

In an embodiment, the decoder 1312 may use a feedback controller 1324 to monitor the response of the output device, compare it to, e.g., a predicted intended movement, and recalibrate the decoder 1312 accordingly. The feedback controller 1324 may include a training program to update a loss function variable used by the decoder 1312.

Some error may be corrected as the subject learns to compensate for the system response based on feedback provided by watching the response of the output device. The degree of correction due to this feedback response, and hence the amount of recalibration that must be shouldered by the system 1300, may depend in part on the degree of plasticity in the region of the brain where the implant 1304 is positioned The subject may be required to perform multiple trials to build a database for the desired cognitive signals. As the subject performs a trial, e.g., a reach task or brain control task, the neural data may be added to a database. The memory data may be decoded, e.g., using a Bayesian algorithm on a family of Haar wavelet coefficients in connection with the data stored in the database, and used to control the prosthetic to perform a task corresponding to the cognitive signal. Other predictive models may alternatively be used to predict the intended movement or other cognitive instruction encoded by the neural signals.

Indeed, there are a wide range of tasks that can be controlled by a prosthetic that receives instruction based on the cognitive signals harnessed in various embodiments of the present invention. Reaches with a prosthetic limb could be readily accomplished. A cursor may be moved on a screen to control a computer device. In another embodiment, the implant may be placed in the speech cortex, such that as the subject thinks of words, the system can identify that activity in the speech center and use it in connection with a speech synthesizer. In this embodiment, a database may first be built up by having a subject think of particular words and by detecting the accompanying neural signals. Thereafter, signals may be read in the speech cortex and translated into speech through a synthesizer by system recognition and analysis with the database. Alternatively, the mental/emotional state of a subject (e.g., for paralyzed patients) may be assessed, as can intended value (e.g., thinking about a pencil to cause a computer program (e.g., Visio) to switch to a pencil tool, etc.). Other external devices that may be instructed with such signals, in accordance with alternate embodiments of the present invention, include, without limitation, a wheelchair or vehicle; a controller, such as a touch pad, keyboard, or combinations of the same; and a robotic hand. As is further described in the ensuing Experimental Results, the system can also decode additional abstract concepts such as expected value. Still further applications for the system of the present invention can be readily identified and implemented by those of skill in the art.

Various implementations of the systems and techniques described here can be realized in digital electronic circuitry, integrated circuitry, specially designed ASICs (application specific integrated circuits), computer hardware, firmware, software, and/or combinations thereof. These various implementations can include one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) may include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Figure 14:
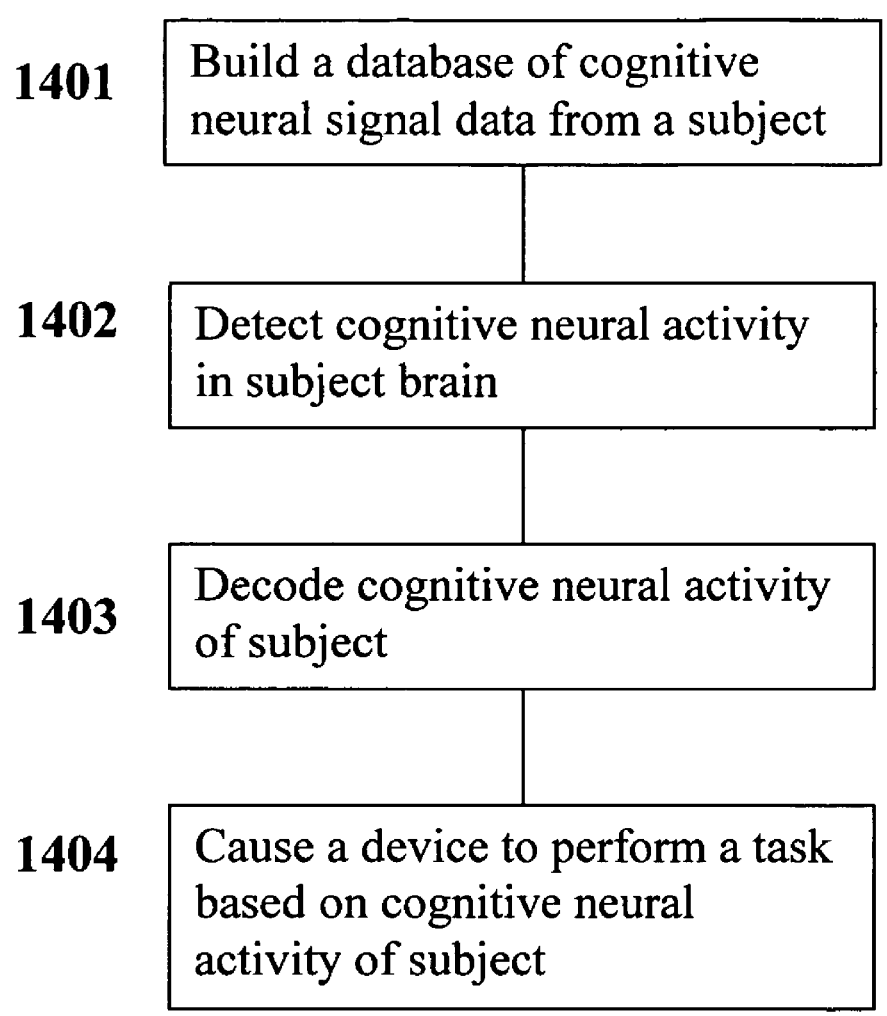
FIG. 14 is a flowchart describing a technique for decoding and controlling a prosthetic utilizing cognitive control signals according to an embodiment of the present invention.

FIG. 14 illustrates one particular logic flow for implementing the system of the present invention. In this embodiment, a database of cognitive neural signal data from a subject may first be built 1401. The database may include neural signal data obtained by way of an implant or any other suitable device that is capable of gathering such information. In one embodiment of the invention, the information itself may relate to the subject's intended movement plan. However, in alternate embodiments the information may relate to a host of other types of data; for instance, intended speech, intended value, or mental/emotional state. Any one form of information may be gathered by an implant or collection of implants; however, in an alternate embodiment, multiple forms of information can be gathered in any useful combination (e.g., intended movement plan and intended value).

In those embodiments of the instant invention in which a database of cognitive neural signal data is compiled from a subject 1401, cognitive neural activity can then be detected from the subject's brain 1402. The cognitive neural activity can be detected by the same or different technique and instrumentation that was used to collect information to build the database of neural signal data 1401. Indeed, in one embodiment of the instant invention, a significant period of time may elapse between building the database and using it in connection with the remaining phases in the system logic 1402, 1403, 1404.

Once cognitive neural activity from the subject brain is detected 1402, the cognitive neural activity may be decoded 1403. The decoding operation may be performed by any suitable methodology. In one embodiment of the present invention, a Bayesian algorithm on a family of Haar wavelet coefficients (as described in greater detail in the Experimental Results, below) may be used in the decode. A device may then be caused to perform a task based on the cognitive neural activity of the subject 1404.

Although only a few embodiments have been described in detail above, other modifications are possible. For example, the logic flow depicted in FIG. 14 does not require the particular order shown, or sequential order, to achieve desirable results.

Experimental Results

The ensuing experimental results describe the detection and decoding of cognitive neural activity information from a group of rhesus monkeys, which is illustrative of particular embodiments and features of the present invention. The system and method of the present invention has many uses beyond those illustrated herein, however, and these experimental results are in no way intended to delineate the extent to which the system and method may find application in connection with neural prosthetic technology.

General

In the experiments, reach goals were decoded from activity present when the monkeys were planning the reach movements, but otherwise were sitting motionless in the dark and were not making eye movements. Thus the cognitive signals in the brain-control task were free of any sensory or motor related activity. Generally only a small number of cells were required for successful performance of the task, with performance increasing with the number of neurons.

For the experiments, single cell and multiunit signals were recorded by a multi-channel recording system (Plexon Inc., Texas) from 96 paralyne-coated tungsten or platinum/iridium electrodes (impedance≈300 kΩ) (Microprobe Inc., Maryland). 64 and 32 electrode arrays were implanted in the medial intraparietal area (MIP, a subdivision of PRR) and area 5 respectively in three rhesus monkeys trained to perform a memory reach task. Area 5 has also been shown to encode movement intention in both eye and limb coordinates. Only cells from MIP were used in 2 monkeys (monkey S and C) while a small minority of area 5 neurons were included for use in the decode in monkey O. One monkey (monkey S) also had 64 electrodes implanted in the dorsal premotor area (PMd) in a separate surgery.

Experiments were initiated two weeks after array implantation. The monkeys were trained in a memory reach task that required them to reach to a flashed peripheral target after a delay of 1.2 to 1.8 seconds. Each experimental session consisted of 250-1100 trials. The median number of trials was 841, 726, and 361 for monkeys S, C and O respectively. Each session was divided into a reach segment for collecting a database and a brain control segment to decode the position of a cursor on a computer screen. Each session started with the reach segment during which monkeys performed thirty memory guided reaches per direction. Specifically, after the monkeys acquired a central red fixation point with the eyes and touched a central green target, a peripheral cue was flashed indicating the location of one out of four, five, six or eight reach targets (as shown in FIG. 1; cue epoch). Reach targets were uniformly distributed around the central fixation point.

As soon as the fixation point and central green target were acquired, hand and eye movements were restricted by a real time behavioral controller (LabVIEW, National Instruments). Eye position was monitored using a scleral search coil (CNC Engineering, monkeys S and O), or an infrared reflection system (ISCAN, monkey C) while hand position was monitored using an acoustic touch screen (ELO Touch). In order to successfully complete a trial, the monkeys were not allowed to move their eyes. In addition, the reaching hand had to be in contact with the centrally located green target at all times except after the "GO" signal which appeared during the reach segment of the session. After the offset of the cue, a delay of 1.5±0.3 seconds ensued. During the reach segment, the green central target was extinguished after the memory period indicating to the animal to reach to the remembered target location (motor epoch). After reaching to the location of the extinguished cue, the monkeys had to maintain contact with the screen for 350 ms. If successful, the cue was illuminated and the monkeys had to maintain contact with the visible target for an additional 300 ms before they were rewarded. Any break in eye fixation during the trial aborted it. If the wrong target was decoded, then monkeys were instructed to reach to the cued location.

In the brain control trials the intended reach location was decoded from a 900 ms interval of the delay period starting 200 ms after cue offset. Unless otherwise noted, all brain control analysis and tuning curves of cells presented herein are based on this 900 ms interval. If the correct position was decoded, the cue location was illuminated with a larger cue and the monkeys received a reward. The monkeys were not allowed to reach or break fixation until after the reward had been delivered. No feedback was given to the monkeys when the wrong target location was decoded. Instead, the green central target was extinguished indicating to the monkeys to initiate a reach. Therefore the monkeys had to continue with a failed decode trial as if it was a reach trial. The adaptive database was not updated after the failed decode trials (see below).

At first glance, it would appear that the retinotopic coding of the plan could be a problem for prosthetic applications when subjects are free to move their eyes. However, the activity within the map of space in PRR is updated with each eye movement to maintain activity for the same locations in extrapersonal space, and the patterns of eye and hand movements are highly coordinated and stereotypical, and eye position signals are present in PRR and may be taken into account by the decode algorithm. As a result, the inventors have found that the intended reaches of animals who are allowed free viewing during reach tasks can also be read out.

Database

Figure 10:
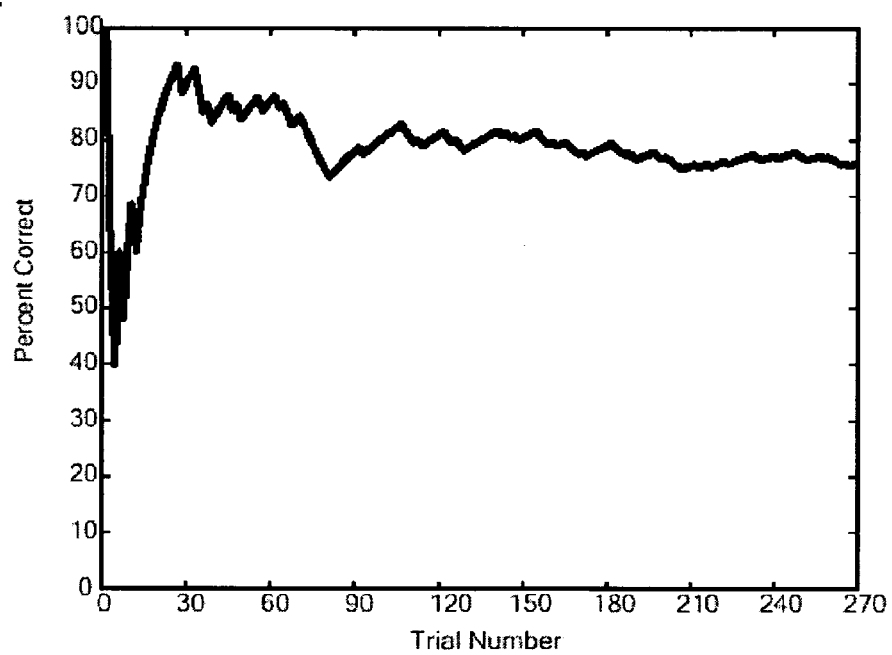
FIG. 10 shows cumulative percent of correctly decoded trials using 700 ms of the motor burst (−100 ms to 600 ms after the "GO" signal in reach trials) of four parietal neurons during reach trials for 1 session in accordance with an embodiment of the present invention.

During the reach trials, the activity of all the cells was recorded and a database containing the firing rates was constructed. Once enough trials were collected (30 reaches for each target location except the PMd recordings which used 20 reaches per target location), the brain control segment of the task was initiated. The goal of this segment was to have the monkeys position a cursor on the screen with their thoughts. A selection of single and multiunit activity was then chosen from the database predicated on their tuning properties assessed using an analysis of variance (ANOVA) on the spiking activity during a 900 ms interval of the memory period beginning 200 ms after cue offset. Many more neurons than those chosen were recorded from the arrays. For example, many cells exhibited strong visual and motor related activity. This activity was also tuned and can easily be used to decode target location with a high success rate (FIG. 10). However, the goal was to decode intentions represented by cognitive signals and not responses directly elicited by stimuli or neural activity associated with overt movements. Therefore, only those neurons that showed clear tuning in the memory period as assessed by the ANOVA were chosen for the decode (monkey S (parietal): range=[5, 13], median=6; monkey C: 3 range=[4, 48] median=6.5; monkey O: range=[6, 10], median=7.5; monkey S (premotor): 3 sessions using 8, 15 and 16 neurons, median=15). For the first 5 sessions of monkey C, the results of the ANOVA were not utilized, instead 48 channels were used for the decode.

Adaptive vs. Frozen Databases

Neural data recorded during successful reaches were added to a database to be used in the brain control segment. On different sessions, the database was either frozen at the end of the reach session, or updated after successfully decoded brain control trials.

Most sessions were run using the adaptive database but, on occasion, the frozen database was used (189 adaptive, 10 frozen). The adaptive database was simply a fixed (30 trials per direction) database moving in time. The database was continuously updated with new successful trials while old trials were removed using a first-in-first-out rule. This way, the database always contained the latest 30 successful trials per direction. The frozen database was composed of the trials collected during the reach segment of the session. Thereafter, the database was not updated but was frozen in time. Off-line analysis indicated that no advantage was gained by using either approach (FIG. 2). Mean success rate for monkey S for all sessions achieved using the adaptive decode (mean±standard deviation) is 43.3±11.1% while the success rate using the frozen database is 42.1±11.7%. The two distributions are not statistically different. This result implies that high level cognitive signals can be decoded using simple algorithms.

Decode Algorithm

The movement intention that was encoded by the neural activity in the memory period for each trial in the brain control task was decoded using a Bayesian algorithm on a family of Haar wavelet coefficients. Bayes rule is defined by $$P(s \mid r) = \frac{P(r \mid s)P(s)}{P(r)}$$

where r is the response and s is the target direction. $P(s|r)$ was calculated for all directions and the direction decoded taken to be the maximum of all $P(s|r)$. One hundred wavelet coefficients were calculated by projecting the spike train recorded during 900 ms of the memory period onto a family of Haar wavelet functions. In this way, temporal features in the spike train that cannot be described by the number of spikes in the memory period (equivalent to firing rate) were exploited.

Haar wavelets are defined by:

$$\psi(t) = \begin{cases} 1 & \text{if } 0 \leq t \leq 1/2 \\ -1 & \text{if } 1/2 \leq t \leq 1 \\ 0 & \text{otherwise} \end{cases}$$

where dilations and translations of $\psi$ generate the orthonormal basis:

$$\psi_{j,n}(t) = \frac{1}{\sqrt{2^j}} \psi\left(\frac{t - 2^j n}{2^j}\right)$$

where j and n are integers that represent the frequency content of the wavelet. Note that the zeroth wavelet coefficient (j, n, t=0) is simply the number of spikes in the 900 ms portion of the memory epoch used in the decode, because the wavelet being projected onto it is the step function.

The Haar wavelets improved the Bayesian decode by taking advantage of the temporal features of the spike train in the memory period. Although a large number of coefficients were calculated, only a few (usually less than five) had relevant information. The optimal coefficients can be calculated by applying sorting algorithms to the coefficients based on information theory.

Off-line decode on 10 sessions using a Bayesian algorithm with wavelets yielded a performance that was on average 6.6±2.9% better than off-line decode that did not use the wavelets (range=[−0.4 9.1]). The number of spikes in the memory period (zeroth wavelet coefficient) yielded the greatest amount of information about the intended goal. The first wavelet coefficient also yielded tuned information useful for decode. The significance of this coefficient implies that the delay period had a different rate at the first and second half of the memory period that was useful for decoding.

The inventors used 50 reaches per direction to build the database for the off-line decode. Not only did the decode performance improve using a greater number of neurons, but it also improved by using a greater number of trials in the database (87% for 8 targets using all 16 neurons; not shown). However, for the 4 target decode, which is the main experimental condition used in this study, 30 reaches per direction was optimal as indicated by off-line simulations.

Off-line decode results suggest that the performance can also be improved using larger training sets with a Fisher linear discriminant (FLD) algorithm. Using data obtained during brain control trials to run off-line decodes, FLD improved the decode by 8.7±6.2% (mean±standard deviation). However, the inventors did not to use this algorithm on-line because the number of trials needed in the training set that would yield a decode performance better than the Bayesian algorithm approached 100 reaches per direction. This would substantially reduce the number of decode trials and was not even possible for some six target sessions. The use of a database with a small number of trials is believed to be more advantageous for neural prosthetics because patients do not need to be burdened with prolonged training sessions.

Although many neurons were tuned during the visual and/or motor epoch of the task, they were not used during brain control trials unless they showed significant tuning during the memory period as assessed using ANOVA. These results demonstrate that high level cognitive signals in PRR are a viable source of control for cortical prosthetics. Table 1 describes the overall performance of three monkeys across all sessions. This table includes all trials from all sessions, from the period when the monkeys were first learning the task until they were very proficient several weeks later. It also includes days when the monkeys were less motivated to work. Thus the table results are not indicative of a highly trained monkey that is highly motivated; under such conditions the monkeys' performance was much better.

TABLE 1

|  | Monkey S | NS | Monkey C | NS | Monkey O | NS |
|---|---|---|---|---|---|---|
| 4 Targets | 45.0 (10.5) | 62 | 34.2 (5.0) | 81 | 43.2 (17.1) | 13 |
| 5 Targets | 48.1 (7.3) | 10 | 30.6 (2.9) | 7 | 59.3 (0.2) | 2 |
| 6 Targets | 37.1 (11.1) | 10 | 25.6 (5.8) | 2 | 31.2 (14.7) | 6 |

Figure 3:
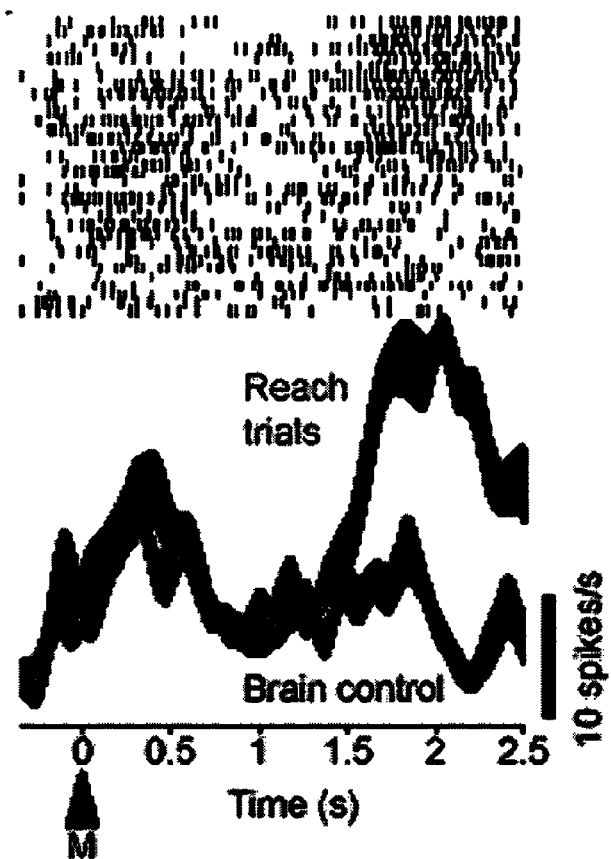
FIG. 3 is a plot showing a comparison of neural activity during reach and brain control trials in accordance with an embodiment of the present invention. Each row is a single trial aligned to the beginning of the memory period. Thickness of the post-stimulus-time histogram (PSTH) represents the standard error calculated with the bootstrap method. M, start of memory period; Sp, spikes.
Figure 4:
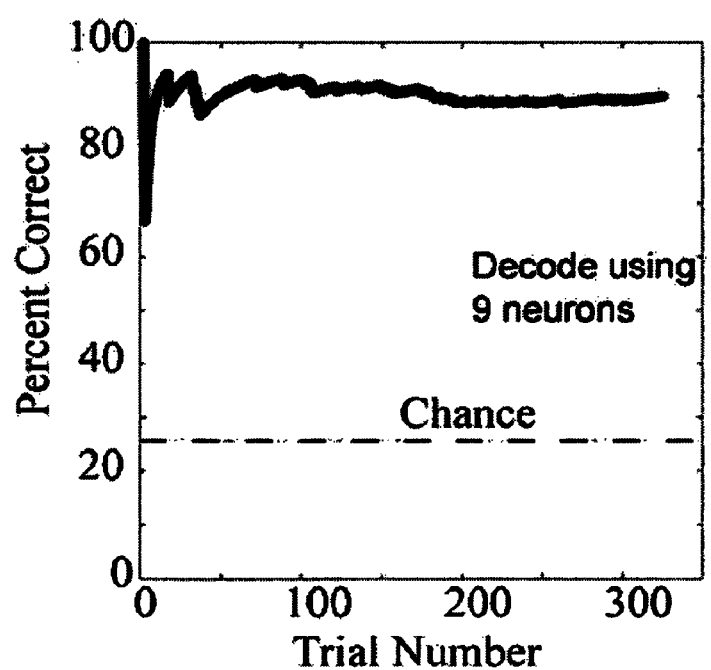
FIG. 4 is a plot showing cumulative decode performance of monkey S during brain control trials in accordance with an embodiment of the present invention. Decode based on memory period activity 200 ms after cue offset. Decode was based on cognitive signals without visual or motor activity. Dashed line indicates chance performance. This illustrates that goal can be decoded with a high success rate.

The use of memory period activity ensured that only the monkeys' intentions were being decoded and not signals related to motor or visual events. An example of the absence of motor related signals during brain control trials can be seen in FIG. 3. The memory activity of this cell is present for both reach and brain-control trials but the motor burst is absent during successfully decoded brain control trials (black). A representative performance of on-line cursor control using intentional signals from one session is shown in FIG. 4. Using only memory period activity, 90% of over 300 trials were correctly decoded for 4 targets. These decode rates were achieved by decoding the memory activity of nine PRR neurons chosen from many more neurons present on various channels of the arrays.

Figure 5:
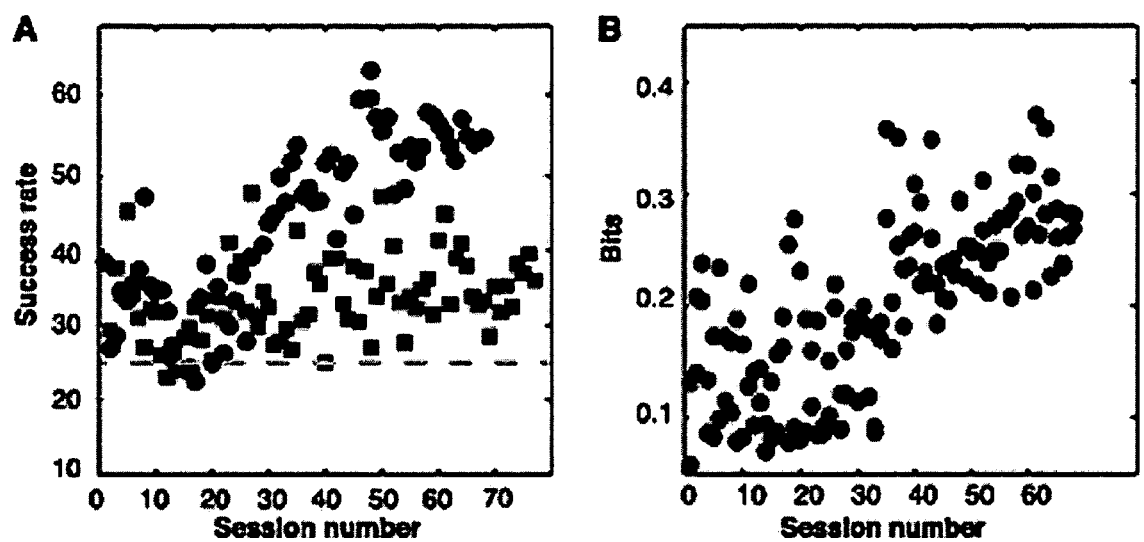
FIG. 5A is a plot showing overall success rates for decoding movement intention from four possible target positions in accordance with an embodiment of the present invention. Circles, monkey S; squares, monkey C. The number of brain control trials varied from 250 to 1100 trials.
FIG. 5B is a plot showing mean mutual information of the cells from monkey S, whose activity was used to build the database (red) and perform the brain control task (black), depicted for all 68 sessions, in accordance with an embodiment of the present invention. For each session, a selection of cells was chosen on the basis of significant tuning. These cells were then used in the brain control trials. The mutual information of these cells was calculated for the 120 reach trials and the subsequent 120 brain control trials.

The performance of all three monkeys is significantly above chance. Examining the sequential performance across sessions also indicates that the animals were able to improve their performance with time. The percentage of trials that were able to be successfully decoded from monkeys S and C for all sessions with four targets (250-1100 brain control trials per session) is shown in FIG. 5A. Not enough sessions were available for monkey O to permit a similar analysis. For both monkeys S and C, the ability to decode their intentions was initially poor, hovering just above chance level. However, it continuously improved over the course of a number of weeks. Regression coefficients for monkey S and monkey C were 0.5 and 0.08 percentage point per session respectively. Both these positive regression coefficients are significant (P<0.01 for monkey S and P<0.02 for monkey C).

Over the course of all the sessions, the amount of information carried by neurons in the brain control task increased more than the amount of information during the reach segment of the task. The mean of the mutual information of the neurons in the memory period during the reach segment and during the brain control segment were calculated for each of the first sixty-eight sessions for monkeys S and C. Data from monkey S is shown in FIG. 5B.

Mutual information is a useful measure as it quantifies the degree of tuning of a neuron as opposed to a statistical p-value which merely provides a probability of whether a neuron is tuned or not (4, 5). The information carried by neurons was calculated using:

$$I(r, s) = \sum P(r, s) \log \frac{P(r, s)}{P(r)P(s)}$$

where s is the target direction and r is the response and the log is base 2. For brain control and reach trials, the mutual information was calculated on an equal number of trials. The joint distribution P(r,s) was estimated using a 2-D histogram between the stimulus and the response. The number of directions in a particular session dictated the number of stimulus bins in the histogram. Eight bins were used for the response which places the histogram outside the sparse region. The marginal distribution of the 2-D histogram was then used as an estimate of the probabilities P(r) and P(s).

This analysis yielded two points per session: the mean information during the reach segment while constructing the database (120 reaches, red points, FIG. 5B) and the information during the initial 120 brain control trials immediately following the reach segment (black dots). During the first twenty sessions, the information about target location is high during reach trials (when the database was being built) and much lower during brain control trials for the same cells. For monkey S (as shown in FIG. 5B), the mean of the difference in the mutual information between the reach and the brain control segments for the first twenty sessions was 0.11±0.002 bits (mean±standard error) and was significantly different from zero (t-test, P<0.01). The difference for the last twenty sessions was 0.028±0.004 bits, also significantly different from zero (P<0.01). However, the difference during the first twenty sessions is significantly greater than the difference from last twenty sessions (P<0.01). Therefore, the information carried by cells recorded during the same session increased more during the brain control segment than during the reach segment over the course of 68 sessions. This effect can also be seen by considering the rate of information increase within the reach and brain control segments. The regression slope for the mutual information during the reach segment was 0.0023±0.0003 bits/session while the slope of the best fit regression line for the mutual information during brain control was 0.0031±0.0003 bits/session. Both these slopes are significantly different from zero (t-test, P<0.01). However, the rate of increase of the information during the brain control segments is greater than the rate of increase during the reach sessions (regression of the difference between reach trials and brain control trials is −0.0018±0.0004 bits/session which is significantly less than zero P<0.01). The same effect was shown by monkey C with less difference (regression of the difference between reach trials and brain control trials is −0.0008±0.0003 bits/session which is significantly less than zero, P<0.01).

Learning Statistics

FIG. 5B shows the mean mutual information from reach and brain control for each of 68 consecutive sessions for monkey S. During the first 20 sessions, the information about target location is high during the reach segment (when the database was being built) and much lower during the brain control segment for the same cells. The mean of the difference in the mutual information between the reach and the brain control segments for the first 20 sessions was 0.11±0.002 bits (mean±standard error) and was significantly different from zero (t-test, P<0.01). The difference for the last 20 sessions was 0.028±0.004 bits, also significantly different from zero (P<0.01). However, the difference during the first 20 sessions is significantly greater than the difference from last 20 sessions (P<0.01). Therefore, the information carried by cells recorded during the same session increased more during the brain control segment than during the reach segment over the course of 68 sessions. This effect can also be seen by considering the rate of information increase within the reach and brain control segments. The regression slope for the mutual information during the reach segment was 0.0023±0.0003 bits/session while the slope of the best fit regression line for the mutual information during brain control was 0.0031±0.0003 bits/session. Both these slopes are significantly different from zero (t-test, P<0.01). However, the rate of increase of the information during the brain control segments is greater than the rate of increase during the reach sessions (regression of the difference between reach trials and brain control trials is −0.0018±0.0004 bits/session which is significantly less than zero P<0.01). The same effect was shown by monkey C with less difference (regression of the difference between reach trials and brain control trials is −0.0008±0.0003 bits/session which is significantly less than zero, P<0.01).

The slope of the performance as a function of session number is 0.48±0.25 percentage points per session for the last 10 sessions which is statistically greater than 0 (p<0.02) (FIG. 5A). This positive slope implies that the performance may have continued to increase if more sessions were performed.

Electromyography

Figure 11:
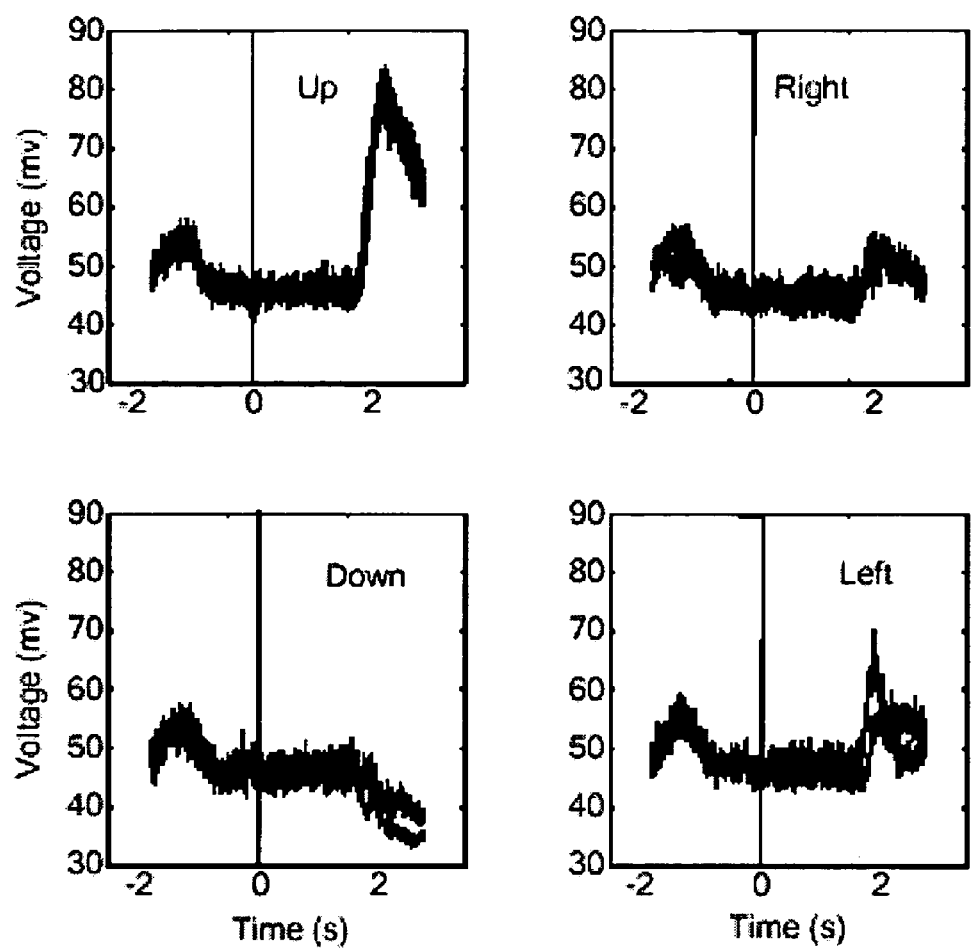
FIG. 11 shows percutaneous EMG recorded from the anterior deltoid of monkey C during reach trials in accordance with an embodiment of the present invention. Black: high reward. Grey: small reward. Plots are aligned to the onset of the cue. Reach directions are indicated on the plot. EMGs were smoothed with a moving window of 10 trials.

Percutaneous EMGs were recorded from the anterior deltoid (FIG. 11), posterior deltoid, the rhombus and the lower trapezius of monkey C over five separate sessions during reach trials. EMG's were low-pass filtered (cutoff 1000 hz), sampled at 2500 Hz and rectified before alignment. If the neural activity of the memory period was related to the direct activation of muscles, then increased EMG should be observed when the monkey is planning a movement in a muscle's preferred direction. Likewise, if the increased direction tuning during preferred rewards is related to muscle activation then there should be an increase in EMG direction tuning for the preferred rewards.

For all individual muscles tested, there was no statistically significant EMG directional tuning in the delay period during brain control trials for either the low or high reward condition. For the anterior deltoid example shown in FIG. 11, the EMGs during the memory period increased by up to 4% when the preferred reward was indicated but this increase was not directionally tuned. Changing the reward had no effect on the activity of the rhombus, posterior deltoid or the trapezium. Thus, the directionally tuned increase in neural activity recorded in the high reward condition during the memory period was not associated with a significant directionally tuned increase in limb EMG.

Variable Reward

Cognitive signals can also relay information about the internal value subjects place on any particular trial. Although expected value related activity had previously not been reported in PRR, experiments were performed to determine whether a cognitive-based prosthetic that can decode reach intention can also decode additional abstract concepts such as expected value. The inventors ran a variant of the memory reach task where cue size indicated the amount, probability, or type of reward monkeys would receive upon completion of a successful trial. Only one aspect of the reward (amount, probability or type) was varied in a single session. Cue size was randomly varied trial-by-trial and the interpretation of cue size was varied across sessions so that a large cue represented the more desirable and less desirable rewards on different days. The mapping of cue size to reward condition had no effect on the representation of expected value. The magnitude of the reward was 0.05 ml and 0.12 ml for low and high volume respectively. When probability was varied, a constant volume reward (0.12 ml) was delivered either 40% or 80% of the time upon successful completion of the trial. Hence, the monkeys were not rewarded on all trials but had to complete all of the trials presented. When reward size or type was varied, reward probability was fixed at 100%. Reward type (orange juice vs. water) was delivered from two sipper tubes that were calibrated to dispense equal volumes of liquid. The sipper tubes were placed near the monkey's mouth with the location of the tube altered on different days. No effect of juice tube placement on the firing rate was found.

Figure 6:
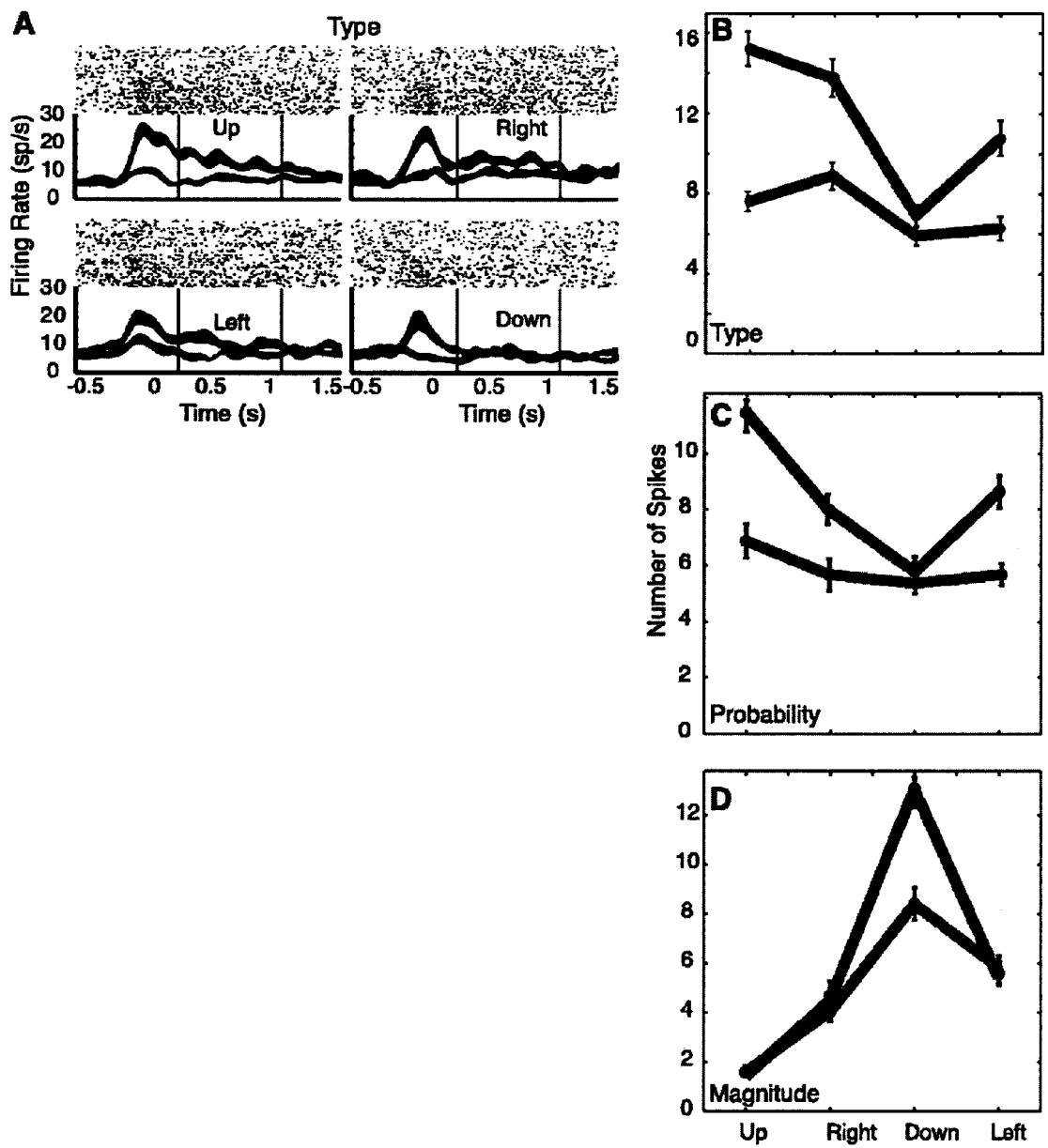
FIG. 6A is a plot showing response of a neuron during brain control trials while reward type was varied in accordance with an embodiment of the present invention; orange juice (black) versus water (red).
FIG. 6B shows its tuning curve. Rasters are aligned to the onset of the memory period. The direction of the intended reach that elicited the responses is written on the figure. Vertical lines superimposed on the PSTH enclose the 900-ms memory segment used to calculate the tuning curves and the duration of the neural activity used to decode reach intention during brain control trials. Volume of juice and water was the same (0.12 ml).
FIGS. 6C and 6D show tuning curve calculated from the firing rates of two additional cells while the probability (6C) and magnitude (6D) of reward was varied in accordance with an embodiment of the present invention.

PRR neurons increased their spatial tuning during brain control and reach trials when the preferred type of reward (orange juice vs. water) was indicated, as shown in FIGS. 6A and 6B. The prior knowledge of a high probability of receiving a reward or the impending delivery of a large volume of reward also increased the tuning of these cells, as shown in FIGS. 6C and 6D. The increased activity during the memory period is not related to an associated increase in muscle activity.

Figure 7:
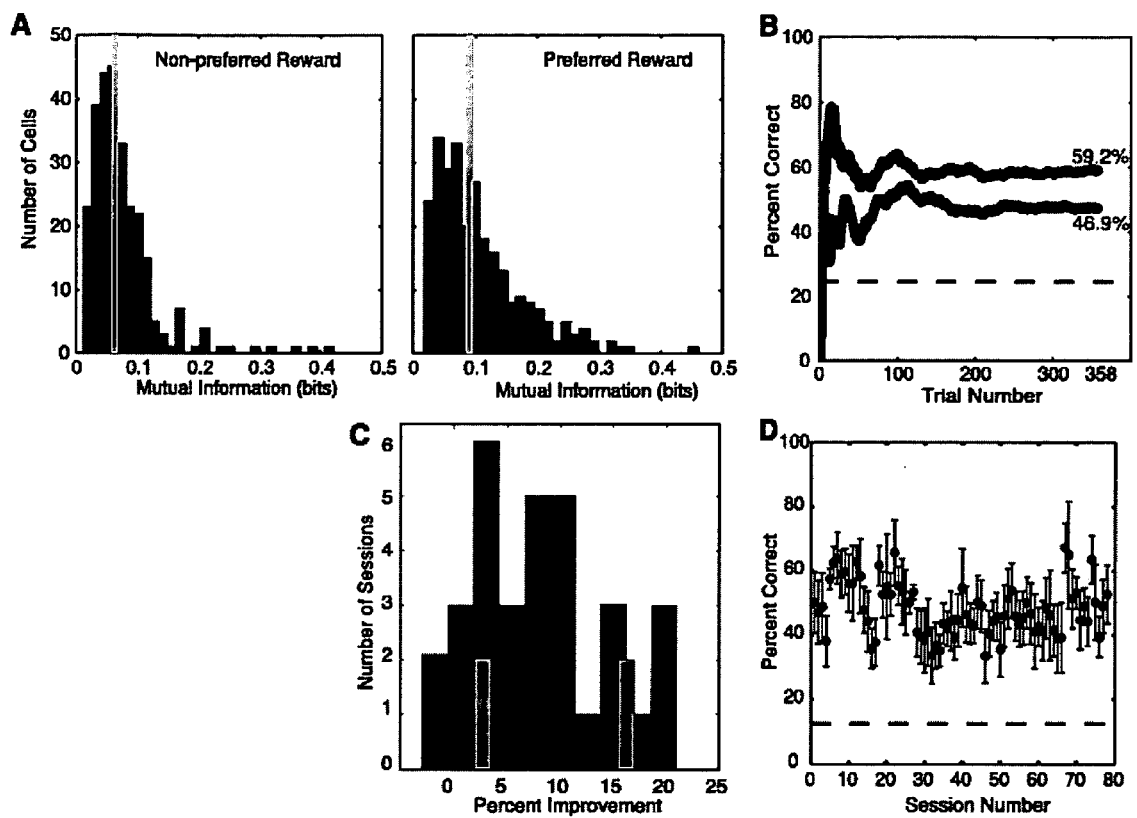
FIG. 7A is a graph showing mutual information for all cells used to decode reach intentions for non-preferred (left panel) and preferred (right panel) rewards during brain control trials for all sessions in accordance with an embodiment of the present invention. Cells for each session are not unique. Grey vertical lines running through the histogram represent the median of the distribution.
FIG. 7B shows the performance of monkey S from one session during preferred (59.2% correct) and non-preferred (46.9% correct) reward conditions in accordance with an embodiment of the present invention. Dashed line represents chance.
FIG. 7C shows improvement in decode between preferred and non-preferred reward in accordance with an embodiment of the present invention. Black, variable magnitude (high volume, 0.12 ml; low volume, 0.05 ml); dark grey, variable type (juice versus water, volume=0.12 ml); light grey, variable probability (high probability=80%, low probability=40%). Total number of sessions is 44 (32 reward magnitude, 4 reward probability, and 8 reward type).
FIG. 7D shows off-line simultaneous decode of four directions and expected value (dashed line shows chance) in accordance with an embodiment of the present invention. Error bars show mean±SD and were obtained by cross-validation (leaving 30 trials out per iteration).

For the brain control trials, those ending with the delivery of the desirable reward carried more information than trials ending in undesirable rewards (non-preferred reward: median, 0.062; 95% confidence interval, 0.0571 to 0.0671; preferred reward: median 0.091; 95% confidence interval, 0.077 to 0.097), as shown in FIGS. 7A and 7B. Accordingly, it was expected that the increased information encoded during the preferred reward condition should also improve the success with which movement intentions could be decoded. Two decodes were run on-line and in parallel during the brain control task; one for the preferred reward and one for the non-preferred reward. Within a given experimental session, a single aspect of the reward (one of size, probability, or type) was varied. The preferred and non-preferred rewards were randomly interleaved on a trial-by-trial basis. An example of a decode performance while reward size was varied is shown in FIG. 7C. The expectation of a high volume of reward improved the overall decode success rate during the brain control segment by 12.2%. Over all the sessions, the increase in the expected value for larger reward volume increased the successful on-line decode of goals by up to 21%, as shown in FIG. 7D, with a median of 8.1% (n=32). The increase in decode performance also occurred when probability (median=10%, n=4) and reward type (median=9%, n=8) were varied. The cells were better tuned during the preferred reward trials thus providing greater information about the target location, exactly the behavior needed to successfully decode a goal.

Figure 8:
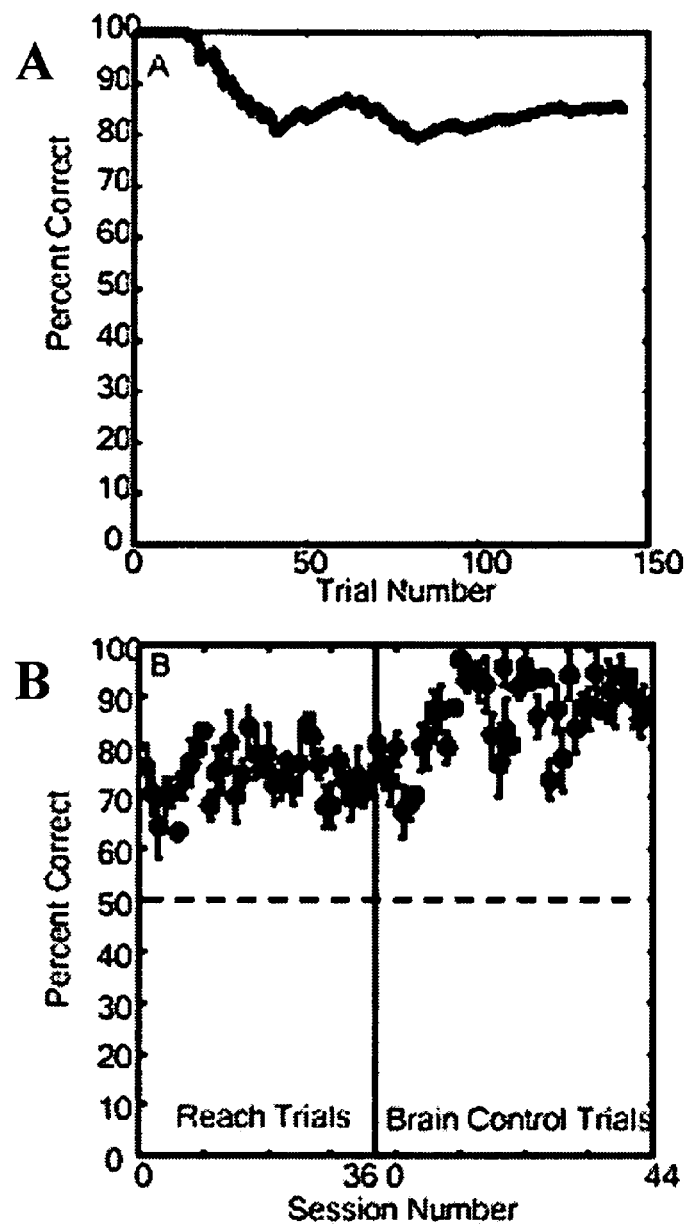
FIG. 8A is a plot showing the decode result of expected value from a single brain control session in accordance with an embodiment of the present invention.
FIG. 8B is a plot showing the decode result for all sessions where expected value of reward was manipulated in accordance with an embodiment of the present invention. Error bars are standard deviation obtained by cross-validation (leaving 30 trials out per iteration). Sessions are not in consecutive order. The first 36 sessions are reach sessions and the last 44 sessions are brain control sessions. Dashed line is chance.

Off-line decodes similar to that used for the goal indicated that the expected value, on a trial-by-trial basis, could be decoded with mean accuracy of 84.7±8.5% in brain control trials, as illustrated in FIG. 8. Even more importantly, expected value and reach goals were simultaneously read out with a mean accuracy of 51.2±8.0% (mean*standard deviation; chance=12.5%), as shown in FIG. 7E.

Reward manipulation also affected behavioral performance. The reaction time from the "GO" signal to the beginning of the movement of all trials during the reach segment of sessions using variable rewards was calculated. The expectation of preferred reward decreased the mean reach reaction time from 320±1.51 ms to 309±1.35 ms (mean±standard error) (FIG. 9). Reaction time is significantly smaller for the preferred reward condition (P<0.01). This enhanced motor performance is consistent with increased motivation.

Expected Value Decode

The expected value of the reward can be decoded, as well. FIG. 8A depicts an off-line decode of expected value of reward type using a frozen database for one brain control session. This binary decode was run independent of reach direction. For the same cells used to decode direction, whether the reward on the current trial is orange juice or water could be correctly identified over 85% of the time (FIG. 8A). Repeating this analysis over all the sessions for monkeys S and C and O, the expected value could be decoded with an overall mean of 80.4±8.6%. For reach trials, decode performance was 74.5±5.2%. For brain control trials, decode performance was 84.7±8.5% (mean±standard deviation) (FIG. 8B).

Decode Interval Length

Figure 12:
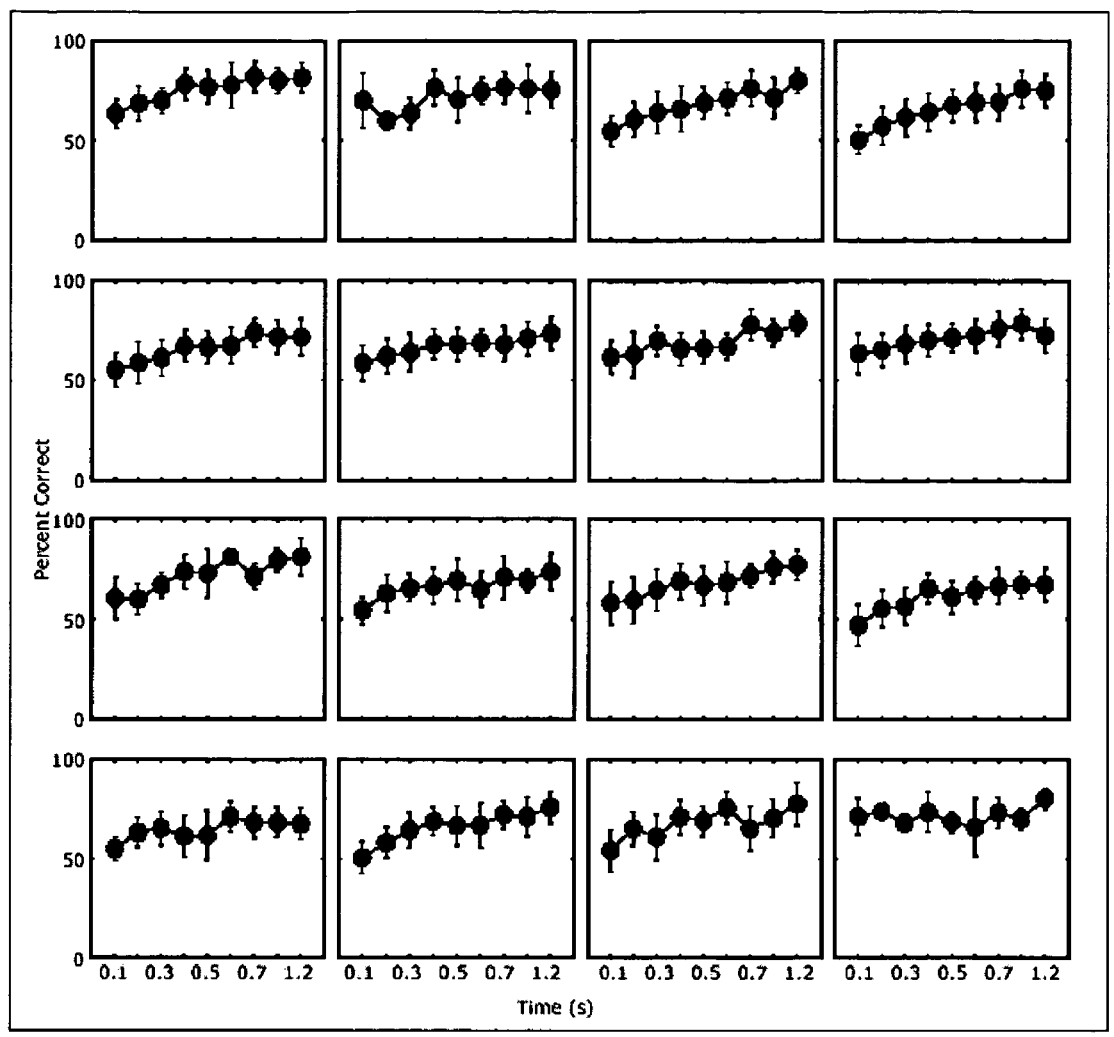
FIG. 12 shows off-line decode on 16 sessions from monkey S using various time interval lengths of the memory period in accordance with an embodiment of the present invention. Note that the time on the x-axis is not continuous but represents the length of the memory period that yielded the corresponding feedback performance. All intervals shown start 200 ms after the offset of the cue and last for the duration indicated on the x-axis. For example, the corresponding y-value at the interval marked 0.2 seconds corresponds to 200 ms of the memory period starting 200 ms after the onset of the memory period (201-400 ms of the memory period).

Off-line decode on brain control trials indicated that memory period intervals as low as 100 ms can yield decode rates that are significantly greater than chance (FIG. 12). There is however a steady increase in the performance as the interval size increased. No conclusion can be made on whether asymptotic behavior was reached because performance continued to increase as the limit of the memory period was reached. Time intervals extracted from the beginning of the memory period yielded better feedback performance than the same sized intervals from latter portions of the memory period (based on off-line analysis on 5 sessions with high performance from monkey S. Brain control performance for 100 ms obtained from the beginning of the memory period was 51.2±4.7% while 100 ms obtained from the end of the memory period yielded a performance of 38.9±7.2% (chance 25%)).

Figure 15:
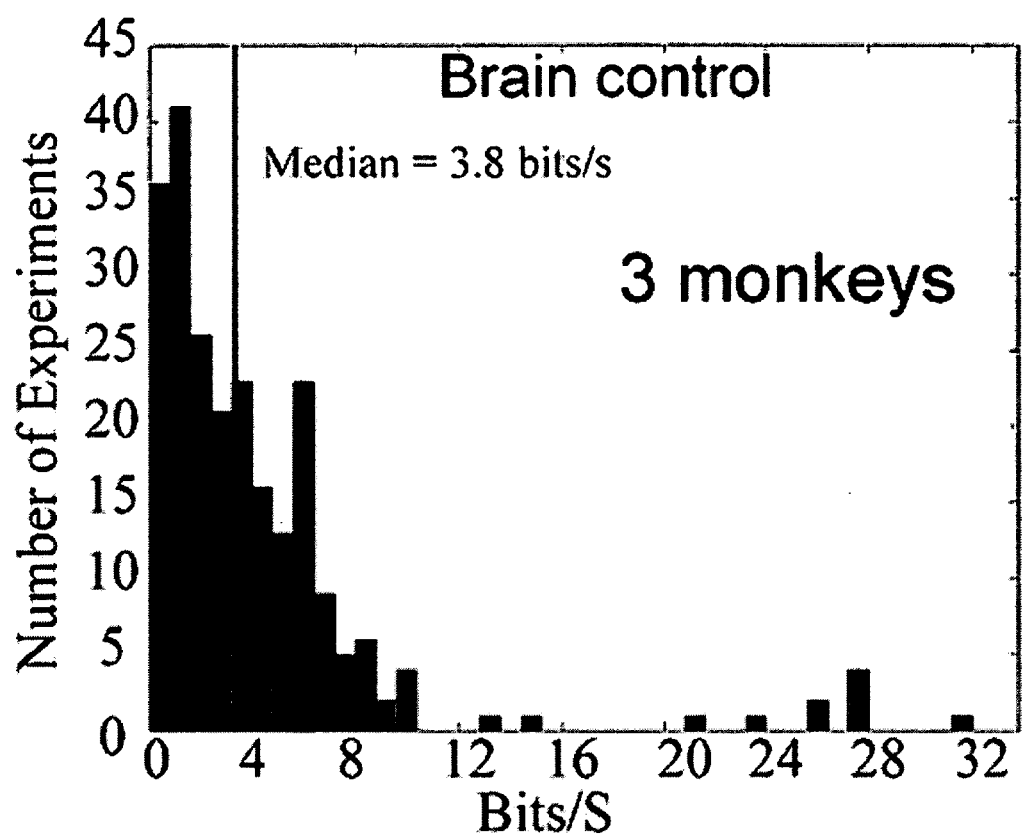
FIG. 15 illustrates the rate of information flow in accordance with an embodiment of the present invention; illustrating that the decoding of goals is much faster than decoding trajectories to a goal. Information contained in 50 ms of the memory period was normalized to 1 second. The plot does not account for the number of neurons used.

The rate of information appears very quickly. FIG. 15 shows that, across all three monkeys and all sessions, the median information rate is 3.8 bits/sec. This value was calculated from 50 msec during the delay period and normalized to 1 second. This result indicates that decoding of goals is much faster than decoding trajectories to a goal (which typically takes about 1 second). Thus the decoding of goals is much faster and will be most ideal when used in prosthetic applications that involve actions akin to typing or the operation of a remote control.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A method, comprising:
   implanting at least one electrode in a brain of a subject;
   receiving electrical signals generated by a plurality of neurons at the at least one implanted electrode, the electrical signals comprising a portion that encodes at least one abstract cognitive concept, the portion of the electrical signals encoding the at least one abstract cognitive concept not encoding either motor movements or intended motor movements, the plurality of neurons having generated the portion of the electrical signals encoding the at least one abstract cognitive concept without having been trained to do so;
   at least partially decoding the at least one abstract cognitive concept encoded in the portion of the electrical signals by generating a feature set based on the electrical signals and mapping the feature set to the at least one abstract cognitive concept using a transformation rule; and
   generating a control signal to instruct an external device to perform a task associated with the at least partially decoded at least one abstract cognitive concept.

2. The method of claim 1, wherein the at least one abstract cognitive concept encoded in the portion of the electrical signals is an intended goal of the subject.

3. The method of claim 1, wherein the at least one abstract cognitive concept encoded in the portion of the electrical signals is an expected value, speech segment, abstract thought, executive control, attention, decision, motivation, memory, imagery, emotion, or mood of the subject.

4. The method of claim 1, further comprising building a database of neural activity data detected from the subject.

5. The method of claim 4, wherein the database comprises information collected from at least one brain control trial performed by the subject.

6. The method of claim 1, wherein at least a portion of the plurality of neurons are located in at least one area of the brain of the subject that generates motor signals.

7. The method of claim 1, further comprising causing the external device to perform the task.

8. The method of claim 1, wherein the external device is a prosthetic limb.

9. The method of claim 1, wherein the external device is selected from a group consisting of a computer device, a speech synthesizer, a wheelchair, a vehicle, a controller, a touch pad, a keyboard, a robotic hand, and combinations thereof.

10. The method of claim 1, wherein generating a control signal further comprises deriving multiple control signals from a single area in the brain or from a simultaneous recording from multiple brain areas.

11. The method of claim 1, wherein generating a control signal further comprises deriving multiple control signals from local field potential ("LFP") recordings, spike activity, or combinations thereof.

12. The method of claim 1, wherein the control signal is an expected value signal.

13. The method of claim 1, wherein the task associated with the at least partially decoded at least one abstract cognitive concept comprises determining the nature of the at least one abstract cognitive concept itself, wherein the at least one abstract cognitive concept is selected from the group consisting of a mood, a motivation, an attention, a preference, a decision, and combinations thereof.

14. The method of claim 1, further comprising improving the subject's control of the external device based on direct effort and learning.

15. The method of claim 1, wherein the at least one abstract cognitive concept encoded by the portion of the electrical signals comprises a preference for a first option over at least one other option, and at least partially decoding the at least one abstract cognitive concept comprises identifying the preference for the first option over the at least one other option.

16. The method of claim 15, wherein the task performed by the external device comprises selecting the first option.

17. The method of claim 1, further comprising:
   deriving the transformation rule by (a) determining a probabilistic relationship between the feature set and the at least one abstract cognitive concept, and (b) minimizing an expected loss which represents a risk associated with incorrectly decoding the at least one abstract cognitive concept to be other than the at least one abstract cognitive concept encoded by the portion of the electrical signals.

18. The method of claim 1, further comprising:
   deriving the transformation rule by (a) constructing a neural network using a training set comprising plural feature sets each associated to an abstract cognitive concept and (b) minimizing an aggregate expected loss for the training set which represents an aggregate risk associated with incorrectly decoding the abstract cognitive concepts from the plural feature sets.

19. A non-transitory machine-readable medium storing machine-executable instructions that when executed by a machine cause the machine to:
   detect neural activity within electrical signals generated by a plurality of neurons that encodes at least one abstract cognitive concept, the detected neural activity being distinguishable from neural activity that encodes information related to both motor movements and intended motor movements, the electrical signals having been received from at least one electrode implanted in at least one area of a brain of a subject, the subject being untrained with respect to generating the detected neural activity;
   generate a feature set for the detected neural activity;
   map the feature set to the at least one abstract cognitive concept using a transformation rule; and generate a control signal to instruct an external device to perform a task associated with the at least one abstract cognitive concept encoded by the detected neural activity.

20. The non-transitory machine-readable medium of claim 19, wherein the at least one abstract cognitive concept encoded in the detected neural activity is an intended goal of the subject.

21. The non-transitory machine-readable medium of claim 19, wherein the at least one abstract cognitive concept encoded in the detected neural activity is an expected value, speech segment, abstract thought, executive control, attention, decision, motivation, memory, imagery, emotion or mood of the subject.

22. The non-transitory machine-readable medium of claim 19, wherein the instructions further cause the machine to build a database of detected neural activity.

23. The non-transitory machine-readable medium of claim 22, wherein the database comprises information collected from at least one brain control trial performed by the subject.

24. The non-transitory machine-readable medium of claim 19, wherein the instructions further cause the machine to cause the external device to perform the task.

25. The non-transitory machine-readable medium of claim 19, wherein the external device is a prosthetic limb.

26. The non-transitory machine-readable medium of claim 19, wherein the external device is selected from the group consisting of a computer device, a speech synthesizer, a wheelchair, a vehicle, a controller, a touch pad, a keyboard, a robotic hand, and combinations thereof.

27. The non-transitory machine-readable medium of claim 19, wherein the instructions to generate the control signal further comprise instructions to derive multiple control signals from a single area in the brain or from a simultaneous recording from multiple brain areas.

28. The non-transitory machine-readable medium of claim 19, wherein the instructions to generate the control signal further comprise instructions to derive multiple control signals from local field potential ("LFP") recordings, spike activity, or combinations thereof.

29. The non-transitory machine-readable medium of claim 19, wherein the control signal is an expected value signal.

30. The non-transitory machine-readable medium of claim 19, wherein the task associated with the at least one abstract cognitive concept encoded by the detected neural activity comprises determining the nature of the at least one abstract cognitive concept itself, wherein the at least one abstract cognitive concept is selected from the group consisting of a mood, a motivation, an attention, a preference, a decision, and combinations thereof.

31. An apparatus, comprising:
a measuring device implantable in a subject;
a database of neural activity data observed in the subject;
an input device operative to receive electrical signals from the measuring device after the measuring device is implanted in the subject, the electrical signals comprising neural activity generated by a plurality of neurons and encoding at least one abstract cognitive concept, the neural activity encoding the at least one abstract cognitive concept being different from neural activity encoding information related to both motor movements and intended motor movements, the plurality of neurons having not been trained to generate the neural activity encoding the at least one abstract cognitive concept;
a signal processor connected to the input device, and operative to analyze the neural activity encoding the at least one abstract cognitive concept to generate a feature set; and
a decoder operative to apply a transformation rule to the feature set that maps the feature set to the at least one abstract cognitive concept encoded by the neural activity, and generate a control signal based on an analytical operation performed with the database of neural activity data from the subject.

32. The apparatus of claim 31, wherein the at least one abstract cognitive concept encoded by the neural activity is an intended goal of the subject.

33. The apparatus of claim 31, wherein the at least one abstract cognitive concept encoded by the neural activity is an expected value, speech segment, abstract thought, executive control, attention, decision, motivation, memory, imagery, emotion, or mood of the subject.

34. The apparatus of claim 31, wherein the database comprises information collected from at least one brain control trial performed by the subject.

* * * * *